(12) United States Patent
Casey et al.

(10) Patent No.: US 11,883,046 B2
(45) Date of Patent: Jan. 30, 2024

(54) SELF-EXPANDING INTRAVASCULAR MEDICAL DEVICE

(71) Applicant: Neuravi Limited, Galway (IE)

(72) Inventors: Brendan Casey, Galway (IE); Aidan Duffy, Galway (IE); Thomas O'Malley, Galway (IE); David Vale, Galway (IE)

(73) Assignee: NEURAVI LIMITED, Galway (IE)

( * ) Notice: Subject to any disclaimer, the term of this patent is extended or adjusted under 35 U.S.C. 154(b) by 23 days.

(21) Appl. No.: 17/586,444

(22) Filed: Jan. 27, 2022

(65) Prior Publication Data
US 2022/0142660 A1   May 12, 2022

Related U.S. Application Data

(63) Continuation of application No. 16/508,029, filed on Jul. 10, 2019, now Pat. No. 11,266,427.

(51) Int. Cl.
*A61B 17/221* (2006.01)
*A61B 17/00* (2006.01)

(52) U.S. Cl.
CPC .. *A61B 17/221* (2013.01); *A61B 2017/00526* (2013.01); *A61B 2017/00867* (2013.01)

(58) Field of Classification Search
CPC . A61B 17/22; A61B 17/22032; A61B 17/221; A61B 2017/00867; A61B 2017/22001; A61B 2017/22034; A61B 2017/22038; A61B 2017/22082; A61B 2017/22094; A61B 2017/2212; A61B 2017/2215; A61B 2090/3966
See application file for complete search history.

(56) References Cited

U.S. PATENT DOCUMENTS

| | | |
|---|---|---|
| 6,551,342 B1 | 4/2003 | Shen et al. |
| 8,066,757 B2 | 11/2011 | Ferrera et al. |
| 8,070,791 B2 | 12/2011 | Ferrera et al. |
| 8,197,493 B2 | 6/2012 | Ferrera et al. |
| 8,784,441 B2 | 7/2014 | Rosenbluth et al. |
| 8,852,205 B2 | 10/2014 | Brady et al. |
| 9,125,728 B2 | 9/2015 | Brady et al. |
| 9,198,687 B2 | 12/2015 | Fulkerson et al. |
| 9,427,300 B2 | 8/2016 | Angel et al. |
| 9,445,829 B2 | 9/2016 | Brady et al. |
| 9,532,792 B2 | 1/2017 | Galdonik et al. |
| 9,532,873 B2 | 1/2017 | Kelley |

(Continued)

FOREIGN PATENT DOCUMENTS

| | | |
|---|---|---|
| WO | 01/19444 | 3/2001 |
| WO | 2012120490 | 9/2012 |

(Continued)

*Primary Examiner* — Jocelin C Tanner
(74) *Attorney, Agent, or Firm* — TROUTMAN PEPPER HAMILTON SANDERS LLP

(57) ABSTRACT

A self-expanding intravascular medical device including a multi-component assembly with a self-expanding outer cage component comprising a plurality of struts; and a single cell wave-shape component disposed within the self-expanding outer cage component forming a channel therein. The proximal end of the single cell wave-shape component is connected to the self-expanding outer cage component at a proximal joint.

14 Claims, 19 Drawing Sheets

(56) References Cited

U.S. PATENT DOCUMENTS

| | | | |
|---|---|---|---|
| 9,533,344 B2 | 1/2017 | Monetti et al. | |
| 9,539,011 B2 | 1/2017 | Chen et al. | |
| 9,539,022 B2 | 1/2017 | Bowman | |
| 9,539,122 B2 | 1/2017 | Burke et al. | |
| 9,539,382 B2 | 1/2017 | Nelson | |
| 9,549,830 B2 | 1/2017 | Bruszewski et al. | |
| 9,554,805 B2 | 1/2017 | Tompkins et al. | |
| 9,561,125 B2 | 2/2017 | Bowman et al. | |
| 9,572,982 B2 | 2/2017 | Burnes et al. | |
| 9,579,484 B2 | 2/2017 | Barnell | |
| 9,585,642 B2 | 3/2017 | Dinsmoor et al. | |
| 9,615,832 B2 | 4/2017 | Bose et al. | |
| 9,615,951 B2 | 4/2017 | Bennett et al. | |
| 9,622,753 B2 | 4/2017 | Cox | |
| 9,636,115 B2 | 5/2017 | Henry et al. | |
| 9,636,439 B2 | 5/2017 | Chu et al. | |
| 9,642,639 B2 | 5/2017 | Brady et al. | |
| 9,642,675 B2 | 5/2017 | Werneth et al. | |
| 9,655,633 B2 | 5/2017 | Leynov et al. | |
| 9,655,645 B2 | 5/2017 | Staunton | |
| 9,655,989 B2 | 5/2017 | Cruise et al. | |
| 9,662,129 B2 | 5/2017 | Galdonik et al. | |
| 9,662,238 B2 | 5/2017 | Dwork et al. | |
| 9,662,425 B2 | 5/2017 | Ilja et al. | |
| 9,668,898 B2 | 6/2017 | Wong | |
| 9,675,477 B2 | 6/2017 | Thompson | |
| 9,675,782 B2 | 6/2017 | Connolly | |
| 9,676,022 B2 | 6/2017 | Ensign et al. | |
| 9,692,557 B2 | 6/2017 | Murphy | |
| 9,693,852 B2 | 7/2017 | Lam et al. | |
| 9,700,262 B2 | 7/2017 | Janik et al. | |
| 9,700,399 B2 | 7/2017 | Acosta-Acevedo | |
| 9,717,421 B2 | 8/2017 | Griswold et al. | |
| 9,717,500 B2 | 8/2017 | Tieu et al. | |
| 9,717,502 B2 | 8/2017 | Teoh et al. | |
| 9,724,103 B2 | 8/2017 | Cruise et al. | |
| 9,724,526 B2 | 8/2017 | Strother et al. | |
| 9,750,565 B2 | 9/2017 | Bloom et al. | |
| 9,757,260 B2 | 9/2017 | Greenan | |
| 9,764,111 B2 | 9/2017 | Gulachenski | |
| 9,770,251 B2 | 9/2017 | Bowman et al. | |
| 9,770,577 B2 | 9/2017 | Li et al. | |
| 9,775,621 B2 | 10/2017 | Tompkins et al. | |
| 9,775,706 B2 | 10/2017 | Peterson et al. | |
| 9,775,732 B2 | 10/2017 | Khenansho | |
| 9,788,800 B2 | 10/2017 | Mayoras, Jr. | |
| 9,795,391 B2 | 10/2017 | Saatchi et al. | |
| 9,801,980 B2 | 10/2017 | Karino et al. | |
| 9,808,599 B2 | 11/2017 | Bowman et al. | |
| 9,833,252 B2 | 12/2017 | Sepetka et al. | |
| 9,833,604 B2 | 12/2017 | Lam et al. | |
| 9,833,625 B2 | 12/2017 | Waldhauser et al. | |
| 9,993,257 B2 | 6/2018 | Losordo et al. | |
| 10,123,803 B2 | 11/2018 | Ferrera | |
| 2004/0199201 A1 | 10/2004 | Kellett et al. | |
| 2009/0192593 A1 | 7/2009 | Meyer et al. | |
| 2011/0160742 A1 | 6/2011 | Ferrera et al. | |
| 2013/0035628 A1 | 2/2013 | Garrison et al. | |
| 2013/0345739 A1* | 12/2013 | Brady | A61B 17/320725 606/200 |
| 2014/0121672 A1 | 5/2014 | Folk | |
| 2014/0371779 A1 | 12/2014 | Vale et al. | |
| 2015/0112376 A1 | 4/2015 | Molaei et al. | |
| 2016/0143653 A1* | 5/2016 | Vale | A61F 2/013 606/114 |
| 2017/0007264 A1 | 1/2017 | Cruise et al. | |
| 2017/0007265 A1 | 1/2017 | Guo et al. | |
| 2017/0020670 A1 | 1/2017 | Murray et al. | |
| 2017/0020700 A1 | 1/2017 | Bienvenu et al. | |
| 2017/0027640 A1 | 2/2017 | Kunis et al. | |
| 2017/0027692 A1 | 2/2017 | Bonhoeffer et al. | |
| 2017/0027725 A1 | 2/2017 | Argentine | |
| 2017/0035436 A1 | 2/2017 | Morita | |
| 2017/0035567 A1 | 2/2017 | Duffy | |
| 2017/0042548 A1 | 2/2017 | Lam | |
| 2017/0049596 A1 | 2/2017 | Schabert | |
| 2017/0071614 A1* | 3/2017 | Vale | A61F 2/013 |
| 2017/0071737 A1 | 3/2017 | Kelley | |
| 2017/0072452 A1 | 3/2017 | Monetti et al. | |
| 2017/0079671 A1 | 3/2017 | Morero et al. | |
| 2017/0079680 A1 | 3/2017 | Bowman | |
| 2017/0079766 A1 | 3/2017 | Wang et al. | |
| 2017/0079767 A1 | 3/2017 | Leon-Yip | |
| 2017/0079812 A1 | 3/2017 | Lam et al. | |
| 2017/0079817 A1 | 3/2017 | Sepetka et al. | |
| 2017/0079819 A1 | 3/2017 | Pung et al. | |
| 2017/0079820 A1 | 3/2017 | Lam et al. | |
| 2017/0086851 A1 | 3/2017 | Wallace et al. | |
| 2017/0086996 A1 | 3/2017 | Peterson et al. | |
| 2017/0095259 A1 | 4/2017 | Tompkins et al. | |
| 2017/0100126 A1 | 4/2017 | Bowman et al. | |
| 2017/0100141 A1 | 4/2017 | Morero et al. | |
| 2017/0100143 A1 | 4/2017 | Grandfield | |
| 2017/0100183 A1 | 4/2017 | Iaizzo et al. | |
| 2017/0113023 A1 | 4/2017 | Steingisser et al. | |
| 2017/0147765 A1 | 5/2017 | Mehta | |
| 2017/0151032 A1 | 6/2017 | Loisel | |
| 2017/0165062 A1 | 6/2017 | Rothstein | |
| 2017/0165065 A1 | 6/2017 | Rothstein et al. | |
| 2017/0165454 A1 | 6/2017 | Tuohy et al. | |
| 2017/0172581 A1 | 6/2017 | Bose et al. | |
| 2017/0172766 A1 | 6/2017 | Vong et al. | |
| 2017/0172772 A1 | 6/2017 | Khenansho | |
| 2017/0189033 A1 | 7/2017 | Sepetka et al. | |
| 2017/0189035 A1 | 7/2017 | Porter | |
| 2017/0215902 A1 | 8/2017 | Leynov et al. | |
| 2017/0216484 A1 | 8/2017 | Cruise et al. | |
| 2017/0224350 A1 | 8/2017 | Shimizu et al. | |
| 2017/0224355 A1 | 8/2017 | Bowman et al. | |
| 2017/0224467 A1 | 8/2017 | Piccagli et al. | |
| 2017/0224511 A1 | 8/2017 | Dwork et al. | |
| 2017/0224953 A1 | 8/2017 | Tran et al. | |
| 2017/0231749 A1 | 8/2017 | Perkins et al. | |
| 2017/0252064 A1 | 9/2017 | Staunton | |
| 2017/0265983 A1 | 9/2017 | Lam et al. | |
| 2017/0281192 A1 | 10/2017 | Tieu et al. | |
| 2017/0281331 A1 | 10/2017 | Perkins et al. | |
| 2017/0281344 A1 | 10/2017 | Costello | |
| 2017/0281909 A1 | 10/2017 | Northrop et al. | |
| 2017/0281912 A1 | 10/2017 | Melder et al. | |
| 2017/0290593 A1 | 10/2017 | Cruise et al. | |
| 2017/0290654 A1 | 10/2017 | Sethna | |
| 2017/0296324 A1 | 10/2017 | Argentine | |
| 2017/0296325 A1 | 10/2017 | Marrocco et al. | |
| 2017/0303939 A1 | 10/2017 | Greenhalgh et al. | |
| 2017/0303942 A1 | 10/2017 | Greenhalgh et al. | |
| 2017/0303947 A1 | 10/2017 | Greenhalgh et al. | |
| 2017/0303948 A1 | 10/2017 | Wallace et al. | |
| 2017/0304041 A1 | 10/2017 | Argentine | |
| 2017/0304097 A1 | 10/2017 | Corwin et al. | |
| 2017/0304595 A1 | 10/2017 | Nagasrinivasa et al. | |
| 2017/0312109 A1 | 11/2017 | Le | |
| 2017/0312484 A1 | 11/2017 | Shipley et al. | |
| 2017/0316561 A1 | 11/2017 | Helm et al. | |
| 2017/0319826 A1 | 11/2017 | Bowman et al. | |
| 2017/0333228 A1 | 11/2017 | Orth et al. | |
| 2017/0333236 A1 | 11/2017 | Greenan | |
| 2017/0333678 A1 | 11/2017 | Bowman et al. | |
| 2017/0340383 A1 | 11/2017 | Bloom et al. | |
| 2017/0348014 A1 | 12/2017 | Wallace et al. | |
| 2017/0348514 A1 | 12/2017 | Guyon et al. | |
| 2018/0064454 A1 | 3/2018 | Losordo et al. | |
| 2019/0000492 A1 | 1/2019 | Casey et al. | |
| 2020/0297364 A1* | 9/2020 | Choe | A61B 17/221 |

FOREIGN PATENT DOCUMENTS

| | | |
|---|---|---|
| WO | 2017/089424 | 6/2017 |
| WO | 2019/079296 | 4/2019 |

* cited by examiner

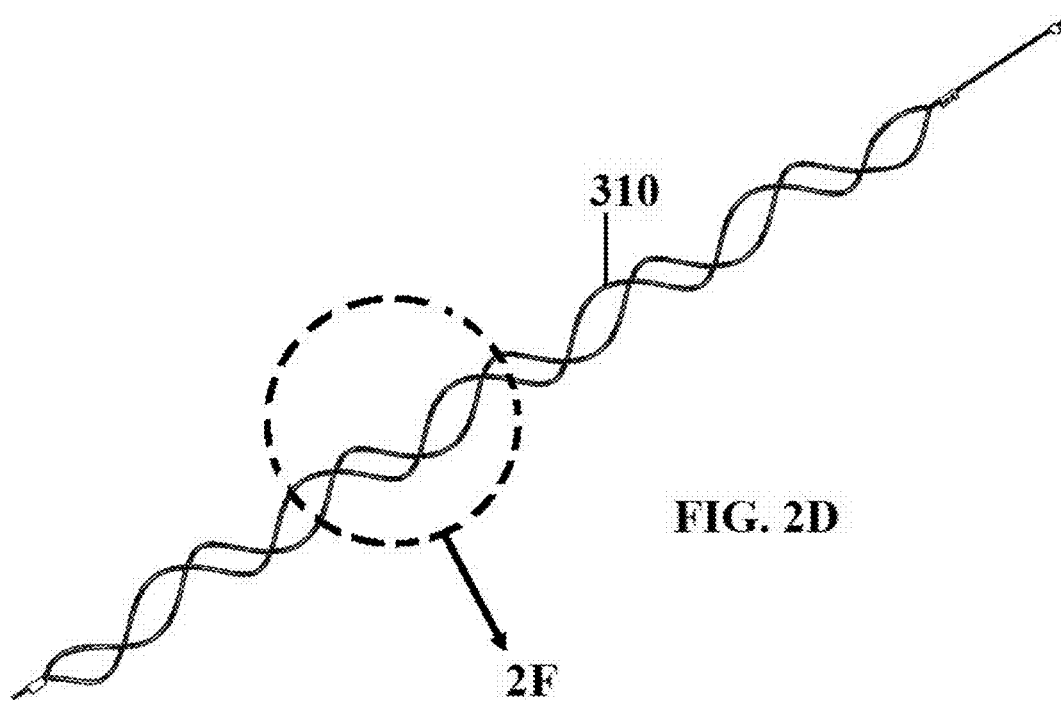
FIG. 2D
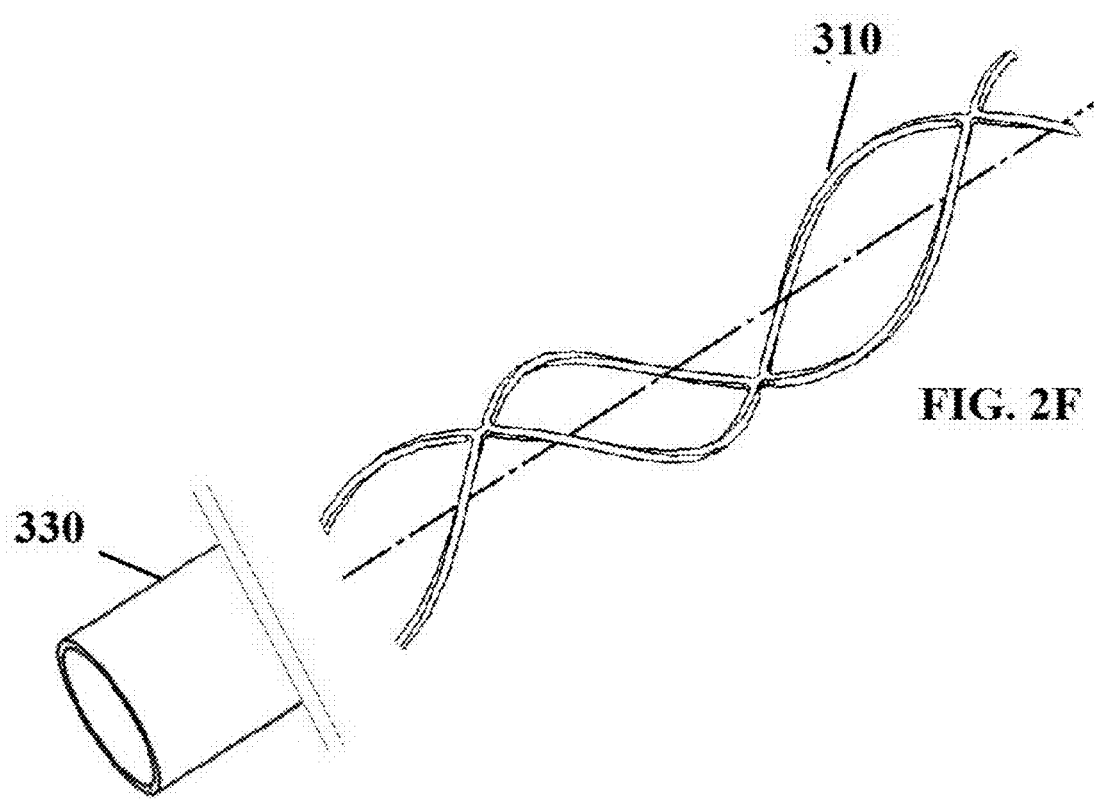
FIG. 2E
FIG. 2F

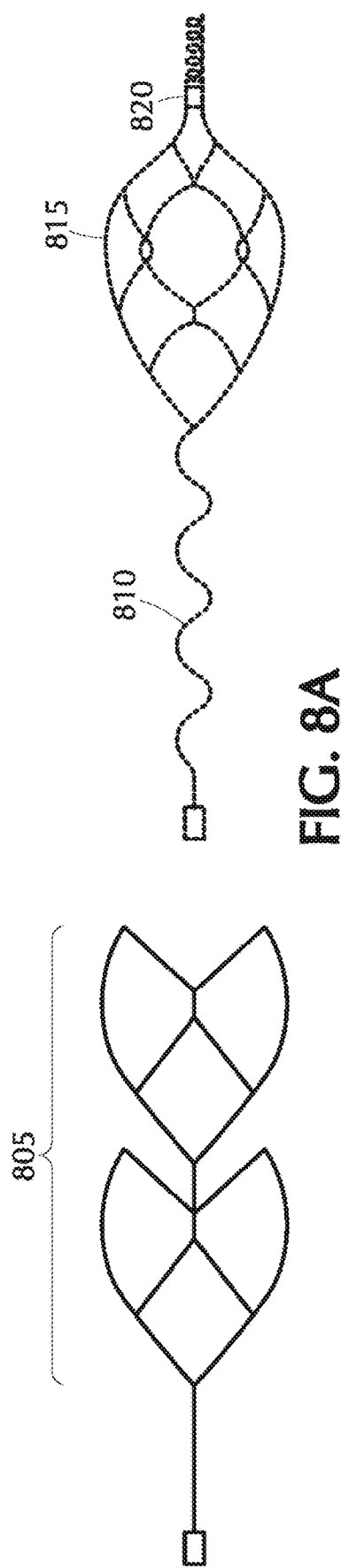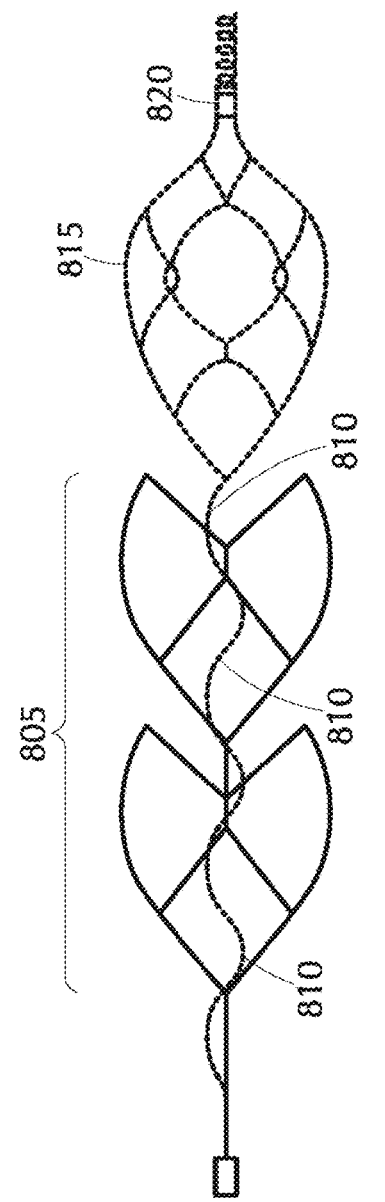
FIG. 8A
FIG. 8B

SELF-EXPANDING INTRAVASCULAR MEDICAL DEVICE

CROSS-REFERENCE TO RELATED APPLICATIONS

This application is a continuation of U.S. Ser. No. 16/508,029, filed on Jul. 10, 2019, which is herein incorporated by reference in its entirety.

BACKGROUND OF THE INVENTION

Field of the Invention

The present invention relates to a self-expanding intravascular medical device. In particular, the present invention is directed to a self-expanding intravascular medical device such as a mechanical thrombectomy device that promotes embedding in the clot, full retrieval of the clot into a catheter, minimizes fragmentation of the clot and other improvements to the overall successful performance of the medical device.

Description of Related Art

Acute ischemic stroke is caused by a thrombotic or embolic occlusion (e.g., blockage) in a cerebral artery which blocks the flow of blood to the brain. The occlusion is typically caused by a blood clot liberated from another part of the body which travels through the vessel and eventually become lodged in the cerebral artery of the brain.

One procedure used to restore blood flow in such conditions is administration of a drug (e.g., a tissue plasminogen activator (tPA)) that helps to dissolve or breakdown the clot. However, the success of restoring blood flow using such a drug alone requires that the medication be given in a relatively short period of time and is suitable only for relatively small clot sizes. Thus, drug treatment is not a viable option in all ischemic stroke cases.

In such other circumstances, a mechanical device is generally deployed intravascularly during a thrombectomy procedure to restore blood flow through the vessel and thereafter physically remove the thrombus, clot, occlusion or blockage into a receiving catheter in a less invasive manner than open surgery. Such mechanical devices may be used alone or in combination with a clot dissolving/busting drug. Typically, the mechanical device used to capture the clot is a self-expanding mesh scaffolding, skeleton, cage or tube (e.g., a stent retriever or stentriever) attached to a wire that is deployed through a catheter to a desired target location.

Thrombectomy treatment or procedure is typically performed on patients within a relative short period of time following a stroke (e.g., less than an approximately 48-hour period after the occurrence of a stroke) and is best suited for large vessel occlusions typically with a diameter greater than approximately 1.0 mm. Non-invasive imaging, for example, MR and non-contrast CT is typically used to determine early ischemic changes in patients to determine if thrombectomy treatment is suitable for that particular patient.

During the thrombectomy procedure or treatment a physician or interventionalist endovascularly introduces a guidewire through the vasculature, typically in an artery located in the groin or arm, or by direct access through the carotid artery. The guidewire is advanced through the vasculature to the target location of the clot, blockage or occlusion. Once the guidewire is properly positioned, a microcatheter with an outer diameter typically less than approximately 1.0 mm, tracks over the guidewire passing through a lumen defined axially through the microcatheter. The guidewire and microcatheter are used to cross the clot or occlusion using standard intervention techniques. While in a compressed state, a stent or mechanical thrombectomy device may be guided through the lumen of the microcatheter to the target site. Upon deployment from the microcatheter the stentriever or mechanical thrombectomy device automatically expands to its original enlarged state. Stentrievers or mechanical thrombectomy devices are typically made of a biocompatible material such as stainless steel, nickel-titanium or tantalum.

It is desirable to develop an improved thrombectomy device with enhanced thrombectomy performance based on one or more factors such as: (i) optimization of embedding of the stent in the clot for clot dislodgement and retention (ii) minimization of clot compression; (iii) minimization of clot fragmentation; (iii) restoration of blood flow; (iv) stabilization of the clot within the stent during retrieval; and (v) reduction of shear force imposed on the clot during retrieval into a catheter. In addition to designing a mechanical thrombectomy device that takes one or more of such factors into consideration, it is also advantageous to design the improved mechanical thrombectomy device to be suitable for use with smaller size catheters.

SUMMARY OF THE INVENTION

An aspect of the present invention is directed to an improved mechanical thrombectomy device having enhanced performance based on one or more of the factors discussed above.

Another aspect of the present invention relates to a self-expanding intravascular medical device including a multi-component assembly with a self-expanding outer cage component comprising a plurality of struts; and a single cell wave shape component disposed within the self-expanding outer cage component forming a channel therein. The proximal end of the single cell wave shape component is connected to the self-expanding outer cage component at a proximal joint.

Still another aspect of the present invention is directed to a self-expanding intravascular medical device having a multi-component assembly including a self-expanding outer cage component comprising a plurality of struts; and an inner component disposed within the self-expanding outer cage component forming a cylindrical channel therein, wherein a proximal end of the inner component is connected to the self-expanding outer cage component at a proximal joint. Each of the self-expanding outer cage component and a circular cross-section of the cylindrical channel formed by the inner component differ in diameter and are formable from a single cut tube or cut pattern, wherein the single cut tube or cut pattern has a primary diameter equal to an expandable diameter of primary struts forming the self-expanding outer cage component while the single cut tube or cut pattern is heat settable to a secondary diameter smaller than the primary diameter to form the circular cross-section of the cylindrical channel formed by the inner component.

Yet another aspect of the present invention relates to a self-expanding intravascular medical device including a multi-component assembly comprising (i) a self-expanding outer cage component comprising a plurality of struts; (ii) a wave shape component disposed within the self-expanding outer cage component; and (iii) an expanded distal closed-end mesh section. The expanded distal closed-end mesh section is attached directly to the wave shape component.

There is no direct physical connection between the expanded distal closed-end mesh section and the self-expanding outer cage component.

While still another aspect of the present invention is directed to a self-expanding intravascular medical device including a self-expanding outer cage component comprising a plurality of struts. Each of the plural struts having a wedge shape radial cross-section having a curved outer surface forming part of an outer diameter of the expandable outer cage and a curved inner surface forming part of an inner diameter of the self-expanding outer cage; wherein a portion of the curved outer surface is removed.

While yet another aspect of the present invention relates to a self-expanding intravascular medical device made from an everted concave sheet or plate cut into a desired pattern comprising a plurality of struts. Each of the plural struts of the everted cut tube has a wedge shape radial cross-section that is widest at a concave inner radial surface and tapers smaller until reaching a concave outer radial surface.

Still another aspect of the present invention is directed to a method for manufacturing a self-expanding outer cage component of a self-expanding intravascular medical device. A desired pattern is cut in a concave sheet or plate. The cut concave sheet or plate is then inverted. Thereafter, the everted cut concave sheet or plate is shape set around a mandrel of a predetermined diameter drawing opposing free edges of the everted cut concave sheet or plate towards one another to form a radial stent comprising a plurality of struts. Each of the plural struts has a wedge shape radial cross-section that is widest at a concave inner radial surface and tapers smaller until reaching a concave outer radial surface.

BRIEF DESCRIPTION OF THE DRAWING

The foregoing and other features of the present invention will be more readily apparent from the following detailed description and drawings of illustrative of the invention wherein like reference numbers refer to similar elements throughout the several views and in which:

FIG. 2D is an isometric view of the single cell wave-shape component of FIG. 2A;

FIG. 2E is an isometric view representational of either the raw material tubing from which the single cell wave-shape component is laser cut or alternatively, the tubular channel formed by the single cell wave-shape component;

FIG. 2F is an enlarged representation of the dashed circular area 2F in the isometric view of the laser cut single cell wave-shape component of FIG. 2D;

FIG. 8A is an exploded view of an exemplary dual structure assembly of the mechanical thrombectomy device in accordance with the present invention having a reduced diameter when compressed or loaded into a catheter;

FIG. 8B is an assembled view of the exemplary dual structure assembly of the mechanical thrombectomy device of FIG. 8A;

DETAILED DESCRIPTION OF THE INVENTION

Figure 1B:
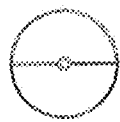
FIG. 1B is an end view of the 2-cell outer cage of FIG. 1A.

The terms "distal" or "proximal" are used in the following description with respect to a position or direction relative to the treating physician or medical interventionalist. "Distal" or "distally" are a position distant from or in a direction away from the physician or interventionalist. "Proximal" or "proximally" or "proximate" are a position near or in a direction toward the physician or medical interventionalist. The terms "occlusion", "clot" or "blockage" are used interchangeably. Furthermore, the term "cell" is the space, region or area that is defined, formed or surrounded by a plurality of adjacent struts (e.g., 4 struts); whereas a "segment" represents a section comprising a number of cells connected by a connector strut.

The self-expanding framework, cage, skeleton or scaffolding designs of the present inventive mechanical thrombectomy device (stentriever) disclosed herein are made from a material capable of recovering its shape automatically once released from a highly strained delivery configuration. A biocompatible superelastic material such as Nitinol or an alloy of similar properties is particularly suitable. The material may be in many forms such as wire, strip, plate, sheet or tube. A particularly suitable manufacturing process is to laser cut a Nitinol tube and then heat-set and electropolish the resultant structure to create an expandable framework, cage, skeleton or scaffolding comprising of struts and connecting elements. This framework may be any of a diverse range of shapes as disclosed herein and may be rendered visible under fluoroscopy through the addition of alloying elements (such as Platinum for example) or through a variety of other coatings or marker bands.

Current self-expanding mechanical stent devices, in particular, mechanical thrombectomy devices (e.g., stentrievers), for use during intravascular medical procedures, such as the medical treatment of acute ischemic stroke, face several challenges or problems when trying to engage and dislodge a target clot, occlusion or blockage and thereafter fully retrieve the clot into an intermediate catheter, guide catheter or sheath under aspiration. The features of the present inventive mechanical thrombectomy device discussed in detail herein overcome such challenges associated with conventional mechanical thrombectomy devices.

One problem addressed by the present invention is that the diameter of the access or intermediate catheter is typically smaller than the diameter of the targeted clot, occlusion or blockage so there is a resistance to clot retraction therethrough and a risk that shear forces may cause the clot to fragment during retrieval. This is an issue with all mechanical thrombectomy devices and shear forces on the clot, occlusion or blockage increase as the diameter of the intermediate catheter decreases. Some clots, occlusions or blockages pose a greater challenge to full retrieval into the intermediate or access catheter such as friable clots which are prone to fragmentation, and organized fibrin rich clots which are less compressible than spontaneous clots.

Figure 1A:
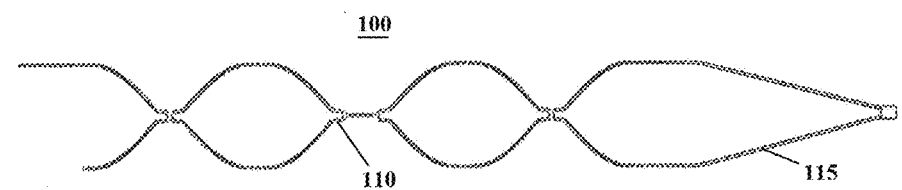
FIG. 1A is a plan view of a 2-cell outer cage of a mechanical thrombectomy device.
Figure 1C:
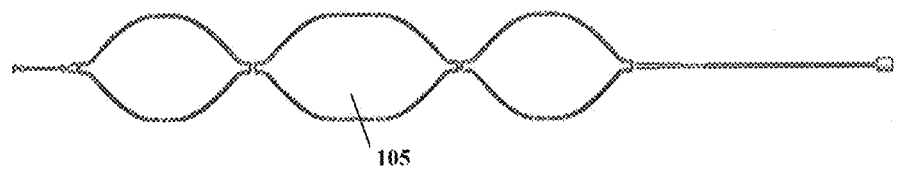
FIG. 1C is a side view of the 2-cell outer cage of FIG. 1A.

It has been discovered through experimental testing that the cut pattern of a mechanical thrombectomy device influences clot embedding and the ability of the device to dislodge and retrieve a clot fully into an intermediate catheter, guide catheter or sheath. In one embodiment of the present invention the mechanical thrombectomy device has a dual structure assembly configuration. An expandable outer cage 100 of the mechanical thrombectomy device, as illustrated in the exemplary plan view depicted in FIG. 1A, has a 2-cell (or 2-segment) pattern but may contain a range of 2-6 cells, wherein the number of cells present in the outer cage is measured in a circumferential direction. The cut pattern forming the outer cage 100 in FIG. 1A has an open strut configuration comprising a minimal number of Nitinol struts to maximize cell area and preferably includes U-shaped crown/saddle points 110 to optimize clot engagement on deployment and improve retention performance and retrieval into the catheter. This open strut configuration minimizes clot compression on deployment thereby minimizing friction between the clot and interior surface of vessel wall. While the relatively large reception spaces 105 (e.g., large cell size or area) allow the clot, occlusion or blockage to embed deeply therein aiding in retraction into the access or intermediate catheter while minimizing clot shear. The crowns 110 also aid in retrieving the clot into the tip of the intermediate or guide catheter. Distal radiopaque coils or markers may be attached to the outer cage to improve visibility of the device during imaging (e.g., fluoroscopy).

The 2-cell configuration of the outer cage has a reduced maximum outer diameter when radially compressed thereby enhancing the wrapping efficiency allowing the device to be loaded and delivered through relatively small size microcatheters with an inner diameter less than or equal to approximately 0.021 inches, preferably less than or equal to approximately 0.017". When loaded into a microcatheter, the 2-cell outer cage configuration ensures a maximum of 4 struts aligned circumferentially side by side in comparison to the typical 4-cell mechanical thrombectomy device having 8 struts aligned circumferentially side by side.

Figures 2A, 2B:
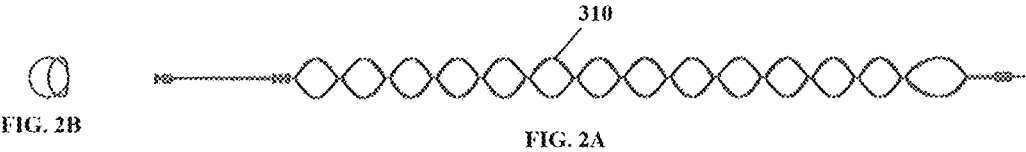
FIG. 2A is a plan view of a single cell wave-shape component of a mechanical thrombectomy device in accordance with the present invention.
FIG. 2B is an end view of the single cell wave-shape component of FIG. 2A.
Figure 2C:
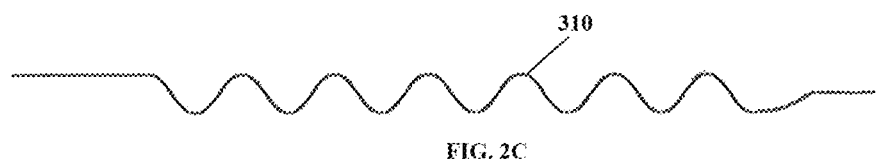
FIG. 2C is a side view of the single cell wave-shape component of FIG. 2A.
Figure 2G:
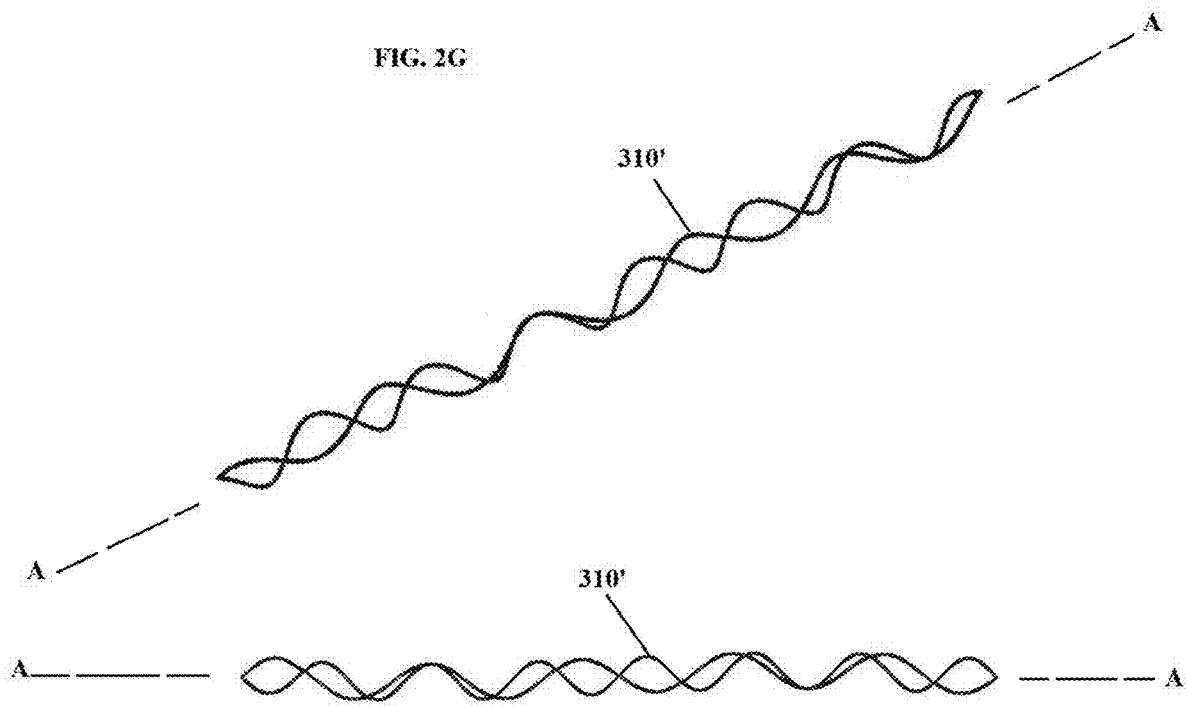
FIG. 2G is an isometric view of an alternative single cell wave-shape component wherein the cell pattern twists or rotates about a central axis extending longitudinally through the component.
Figure 2H:
FIG. 2H is a side view of the single cell wave-shape component of FIG. 2G.

Disposed within the 2-cell outer cage 100 of the dual structure mechanical thrombectomy device is a single cell wave-shape component 310, the single cell configuration being clearly illustrated in the plan view of FIG. 2A and isometric view of FIG. 2D. The wave-shape component 310 may be laser cut from a tube of raw material 330 (FIG. 2E) to form the wave-shape component (FIG. 2F). Alternatively, the wave-shape component may be cut from a smaller diameter tube and expanded to the desired outer diameter. A different configuration of the single cell wave-shape component 310' is shown in isometric and side views provided in FIGS. 2G and 2H, respectively, wherein the cell pattern twists or rotates about a central axis (A) extending longitudinally through the component.

Upon deployment, the wave-shape component 310 opens a channel through the clot facilitating immediate restoration of partial flow of blood through the clot. This channel is evident when viewed end-on and is typically circular in shape when freely expanded, as seen in FIG. 2B. The wave profile of the wave-shape component, as depicted in the side view in FIG. 2C, promotes engagement of the clot on dislodgement and during retention into the catheter. The wave-shape component also stabilizes relatively small and friable clots which migrate fully or partially inside the outer cage 100 during retrieval. The wave-shape component stabilizes the clot minimizing movement to the distal end of the thrombectomy device, where fragments may be lost or captured in the fragment protection zone. In addition, the wave-shape component is also deflectable to the side when clots are being pulled into the intermediate guide catheter. As a result, the wave-shape component enhances performance without inhibiting the ability of the device to retrieve clots into local aspiration or intermediate catheters.

Figure 4:
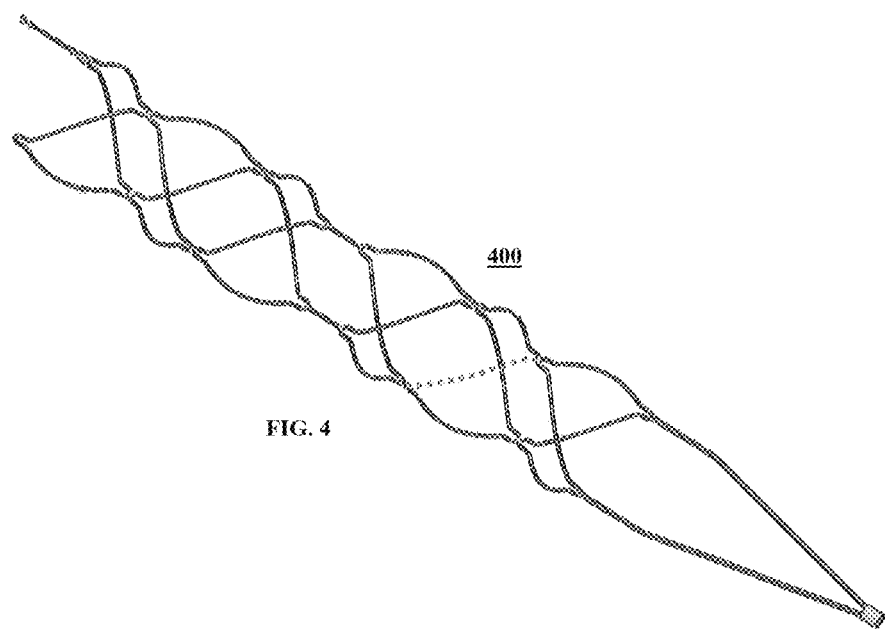
FIG. 4 is an isometric view of an alternative 2-cell outer cage configuration of a mechanical thrombectomy device in accordance with the present invention, wherein one of the primary struts forming the outer cage has been removed (as denoted by the dashed line)
Figure 5:
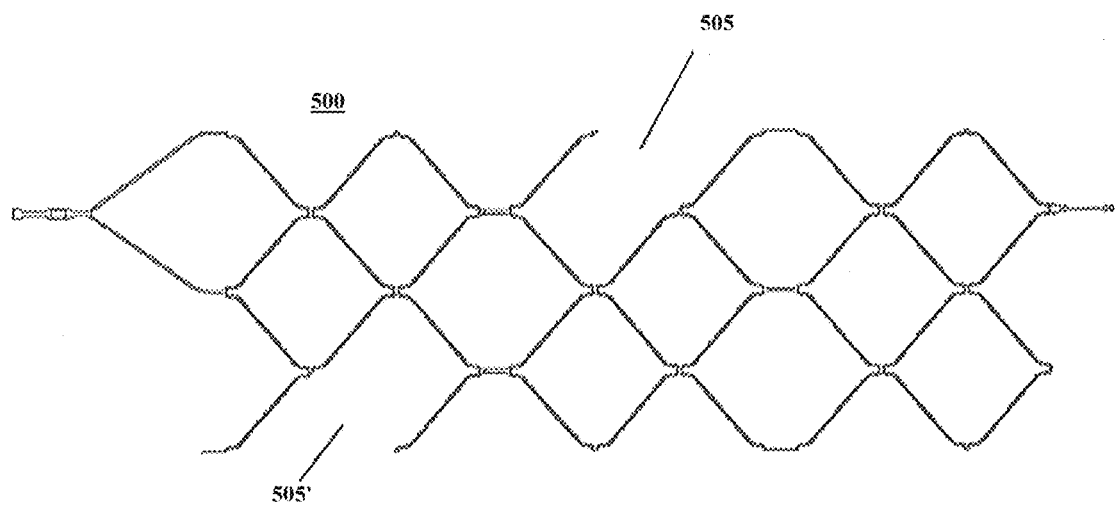
FIG. 5 is a plan view while in an unrolled, flat state of another exemplary 2-cell outer cage mechanical thrombectomy device, wherein two struts have been removed.

To maximize the cell area or clot reception spaces in the outer cage of the present inventive mechanical thrombectomy device and thereby improve embedding of the clot therein, one or more struts may be removed. In the exemplary illustration of the outer cage 400 in an expanded state depicted in the isometric view of FIG. 4, the dotted or dashed line represents a single strut that has been removed from the outer cage. With the removal of one or more struts, the laser cut pattern of the outer cage tubing is no longer symmetrical, i.e., asymmetrical or lacking symmetry. Removal of one or more struts enlarges the cell area and potential reception space for the clot to embed in the outer cage. Such enlarging of spaces allows the clot to embed more deeply and, as a result, minimizes the potential for dislodgement hence increasing the probability of full or entire clot retrieval into the intermediate catheter. However, the laser cut pattern retains sufficient contact with the clot to prevent loss of the clot into a side branch or during retrieval around a challenging bend in the vessel. FIG. 5 depicts in an unrolled state (laser cut pattern) another exemplary embodiment of the outer cage 500 with two struts removed (505, 505') creating two enlarged cells or reception spaces in which the clot may embed. It is contemplated and within the intended scope of the present invention to remove any number of one or more struts from the outer cage.

Figure 3A:
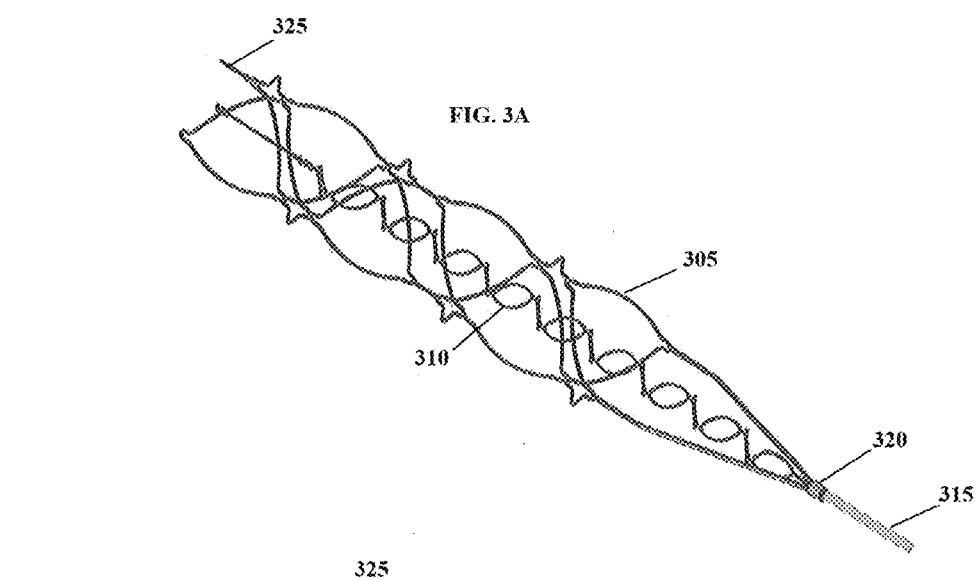
FIG. 3A is an isometric view of a dual structure assembly mechanical thrombectomy device in accordance with the present invention including the 2-cell outer cage of FIGS. 1A-1C and the single cell wave-shape component of FIGS. 2A-2D disposed therein, wherein the distal end of the wave-shape component is attached to the outer cage.
Figures 3B, 3C:
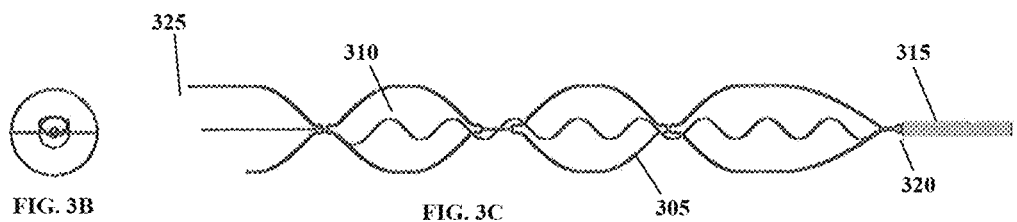
FIG. 3B is an end view of the dual structure assembly mechanical thrombectomy device of FIG. 3A.
FIG. 3C is a side view of the dual structure assembly mechanical thrombectomy device of FIG. 3A.

FIGS. 3A-3C depict an isometric view, an end view, and side view, respectively, of the dual structure assembly of the 2-cell outer cage and single cell wave-shape component, shown in FIGS. 1A-1C and 2A-2D, respectively. The wave-shape component 310 disposed inside the outer cage 305 is connected to the shaft 315 at the proximal joint 320. At an opposite distal end 325, the two components (305, 310) are connected to one another, but may otherwise be free or floating relative to one another.

Figure 3H:
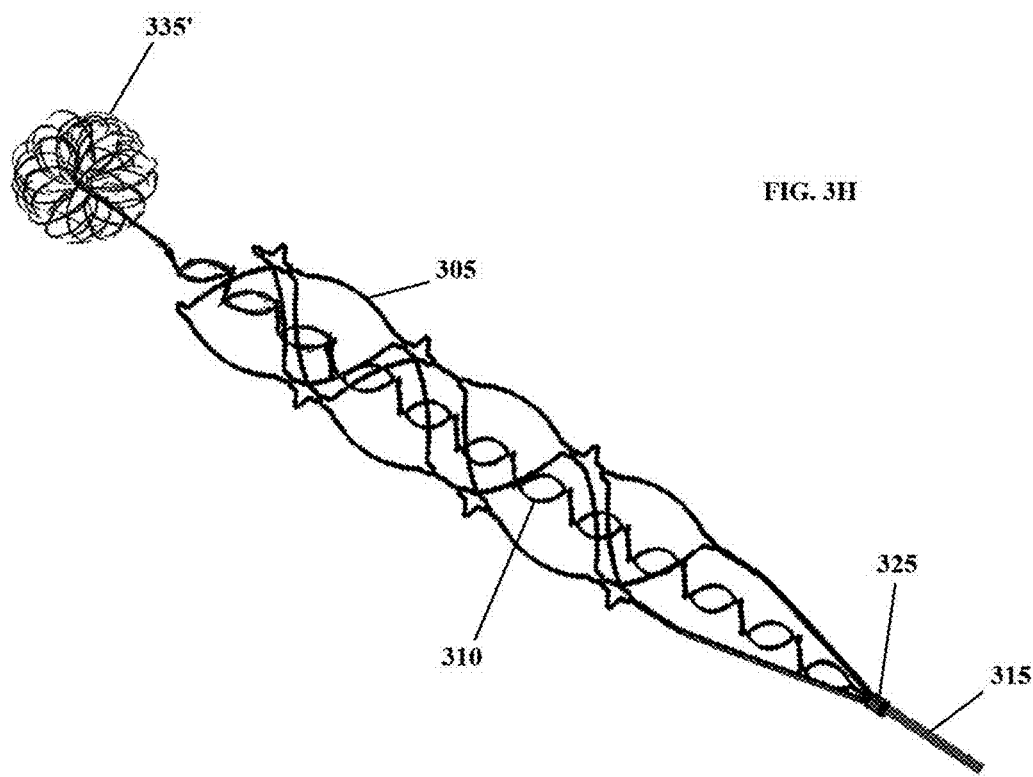
FIG. 3H is an isometric view of distal fragment protection provided by a clump or ball of fibers or wire, wherein the ball is connected to the distal end of the wave-shape component while the distal end of the outer cage remains floating relative to the distal mesh.
Figure 3D:
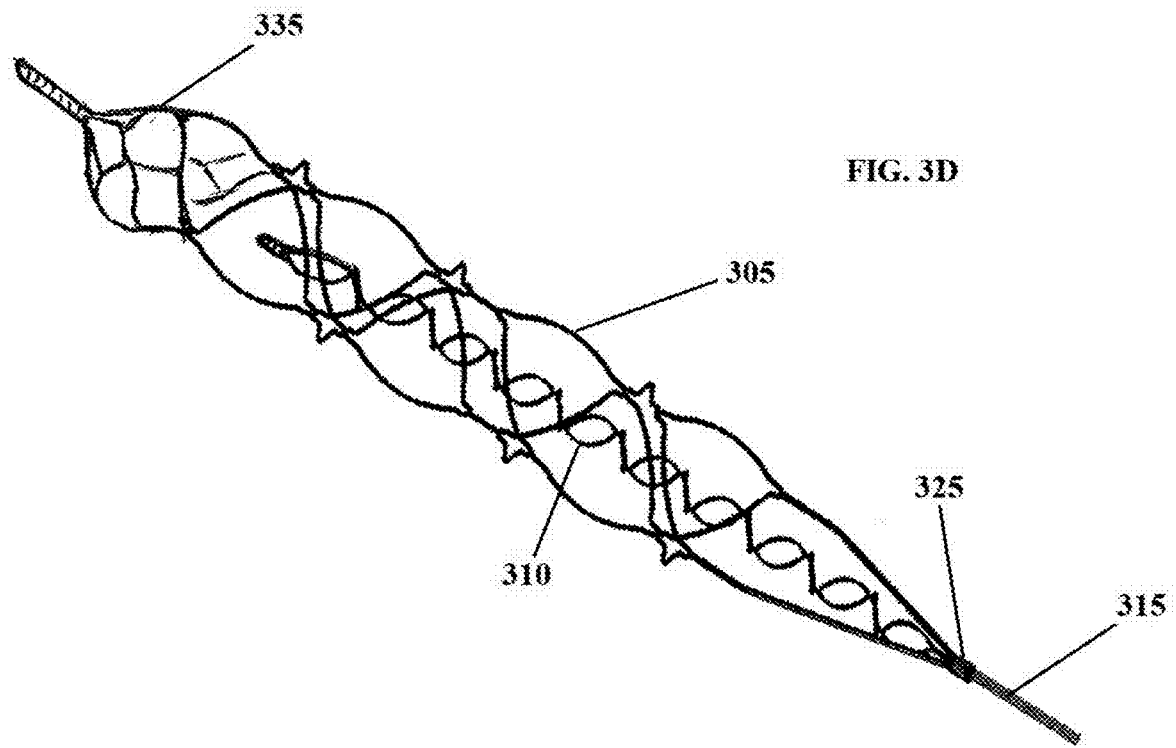
FIG. 3D is an isometric view of an alternative dual structure assembly mechanical thrombectomy device in accordance with the present invention including the 2-cell outer cage of FIGS. 1A-1C and the single cell wave-shape component of FIGS. 2A-2D disposed therein, wherein a distal mesh connected to the distal end of the outer cage provides distal fragment protection and the wave-shape component is floating or free relative to the outer cage.
Figure 3E:
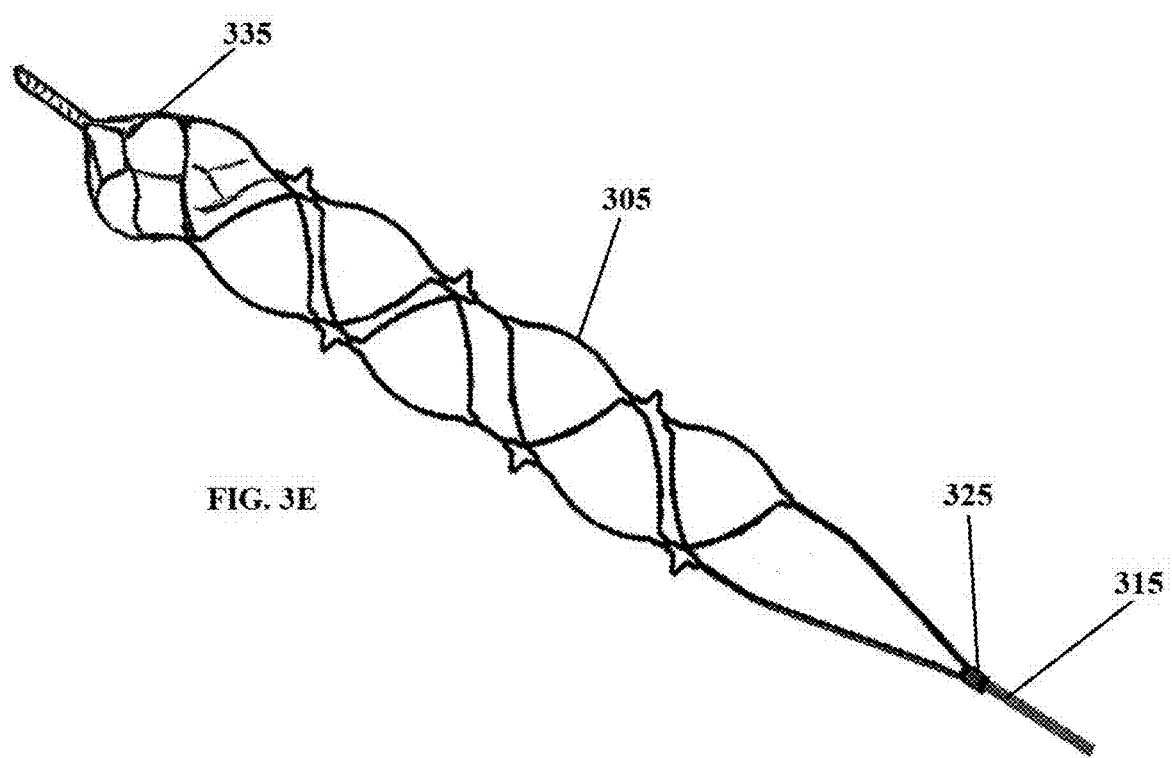
FIG. 3E is an isometric view of the outer cage in FIG. 3D without the wave-shape component.
Figure 3F:
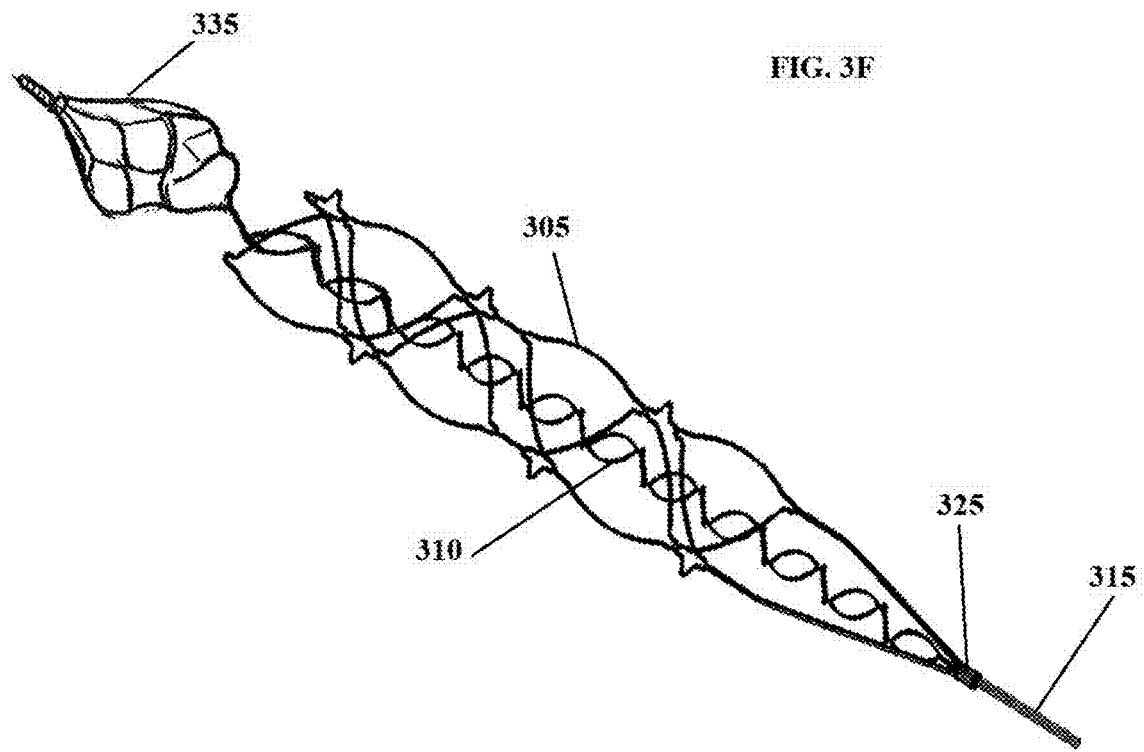
FIG. 3F is an isometric view of fragment protection provided by a distal mesh connected to the distal end of the wave-shape component while the distal end of the outer cage remains floating relative to the distal mesh.
Figure 3G:
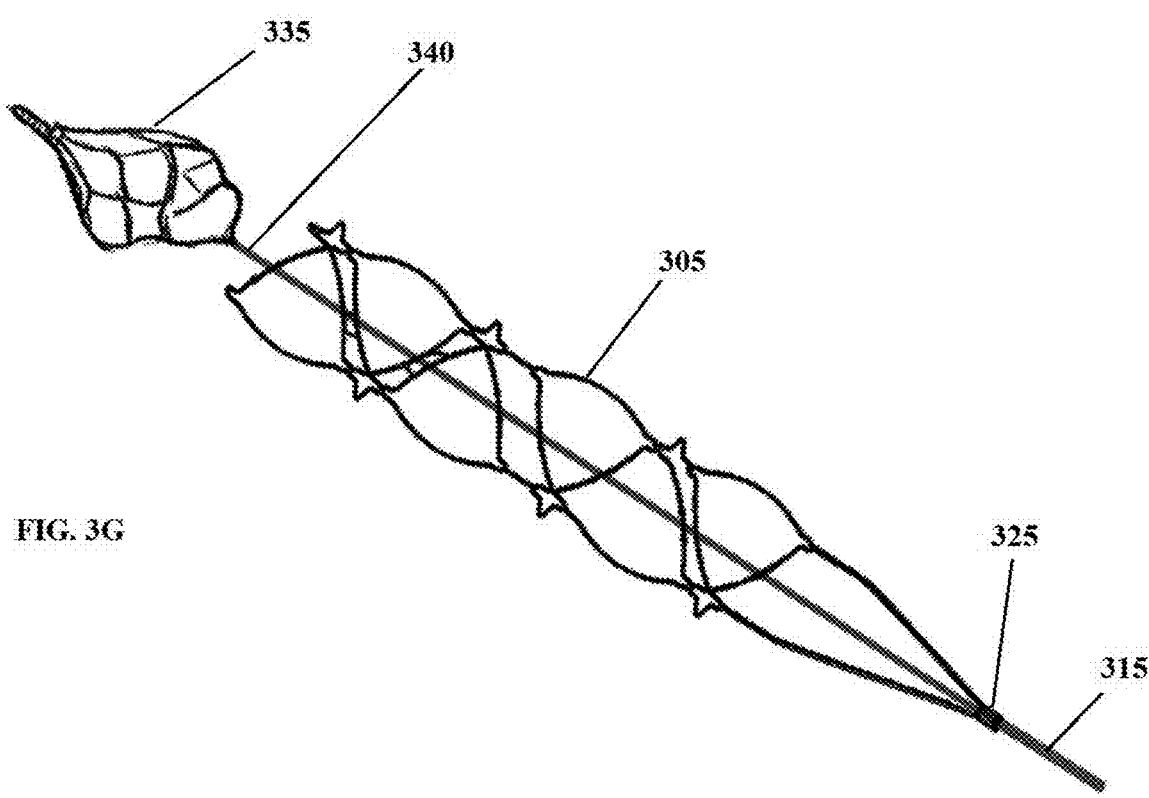
FIG. 3G is an isometric view of distal fragment protection provided by a distal mesh, wherein the wave-shape component has been eliminated, the distal mesh is connected via a wire or extension of the proximal shaft.

A distal fragment protection member may be included in the present inventive mechanical thrombectomy device to provide a distal fragment protection zone. Referring to FIG. 3D, a distal mesh section 335 comprising a plurality of struts heat set in shape to have a tapered distal end and attached to the distal end of the outer cage 305 provides distal fragment protection. Disposed within the outer cage 305 is the wave-shape component 310 whose distal end 325 is floating (e.g., unattached, untethered, unsecured, unconnected) relative to both the outer cage and the distal mesh section. FIG. 3E is an isometric view of the outer cage and distal mesh section of FIG. 3D without the wave-shape component. In still another variation illustrated in FIG. 3F, distal fragment protection is provided by distal mesh section 335 connected to the distal end of the wave-shape component 310 while the distal end of the outer cage 305 is floating, free or unconnected relative to the distal mesh section 335. Whereas, in FIG. 3G, since the wave-shape component has been eliminated, distal mesh section 335 is connected via a wire or extension of the proximal shaft 315. Rather than a distal mesh section being an expanded skeleton having a plurality of struts, distal fragment protection may be provided by a distal clump, ball or sphere 335' of intertwined strands (e.g., biocompatible fibers or wire such as Nitinol wire), as depicted in FIG. 3H. The intertwined strands forming the clump 335' need not necessarily be in the shape of a ball or sphere, but may take on any amorphous or geometric shape. The distal clump of intertwined strands 335' is connected to the distal end of the wave-shape component 310 while the distal end of the outer cage 305 is floating, free or unconnected relative to the distal clump 335'.

Figure 6A:
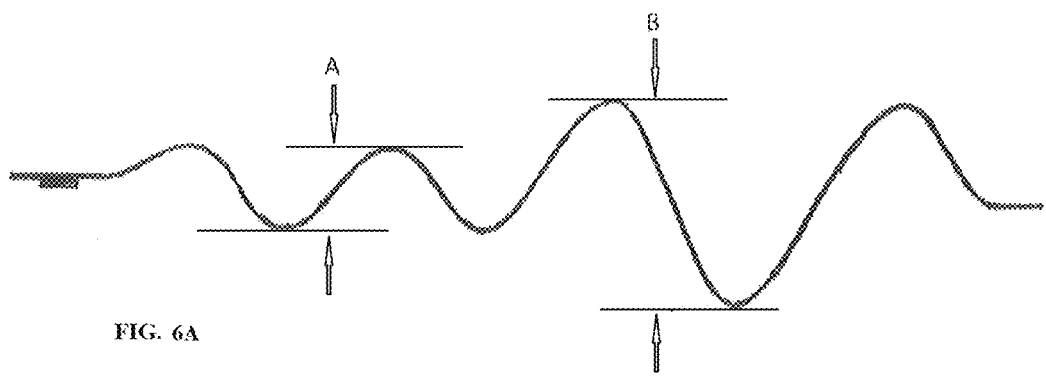
FIG. 6A is a side view of a wave-shape of the single cell wave-shape component of the mechanical thrombectomy device in accordance with the present invention, wherein the wave-shape varies in height along the length of the component.
Figure 6B:
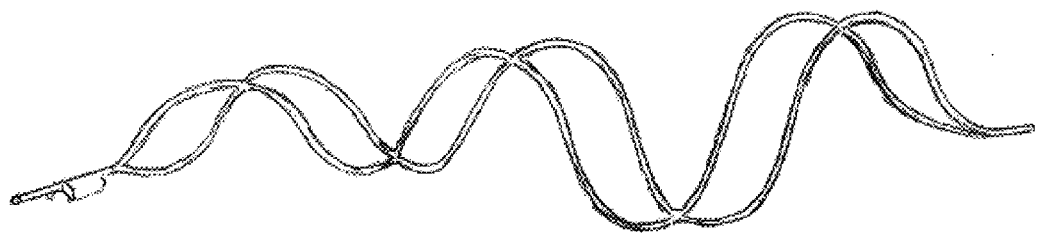
FIG. 6B is an isometric view of one configuration of the single cell wave-shape component of the mechanical thrombectomy device in accordance with the present invention, wherein both the amplitude (height) and corresponding cell size varies along the length of the component.
Figure 6C:
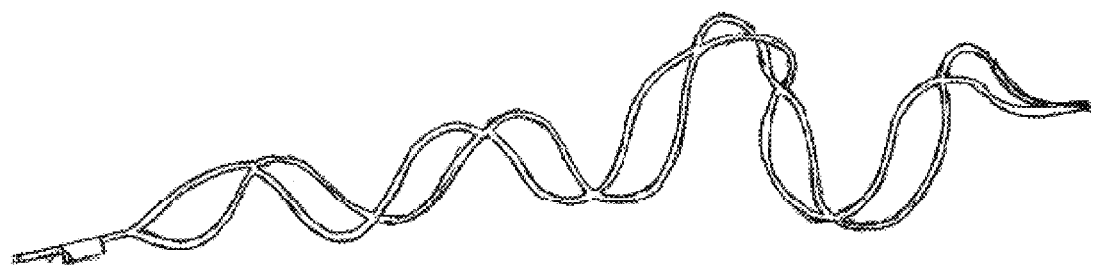
FIG. 6C is an isometric view of another alternative configuration of the single cell wave-shape component of the mechanical thrombectomy device in accordance with the present invention; wherein each cell size is substantially the same, but the substantially uniform cut cells are heat set to a desired shape to produce a varying wave amplitude (height) along the length of the component.

The wave pattern of the wave-shape component 310 may be varied in a number of different ways. In a first configuration shown in the isometric view of FIG. 6B, the tube may be laser cut into cells of different sizes that are then heat set into a variable wave shape whose amplitude (height) varies along the length of the component. Referring to the side view in FIG. 6A, the amplitude (height) "B" is greater than that of the amplitude (height) "A" in the wave shape. In this configuration in which the wave shape varies in both amplitude (height) and corresponding cell size or length, crowns at the connection points between cells are positioned at the peak and trough of each wave. Another possible configuration of the wave shape is shown in FIG. 6C, wherein the tube is cut into cells substantially uniform in size and then heat set to produce a varying wave amplitude (height) along the length of the wave-shape component. Unlike the embodiment in FIG. 6B, crowns at the connection points between cells in the wave-shape component structure in FIG. 6C are not always positioned at the peak or trough of each wave.

More connection points and hence more crowns are present in the configuration of FIG. 6C promoting engagement with the clot. Variation in amplitude and/or length of the single cell of the wave-shape component provides additional protection against fragmentation of the clot and, when assembled within the outer cage, optimizes clot stabilization performance.

Figure 7A:
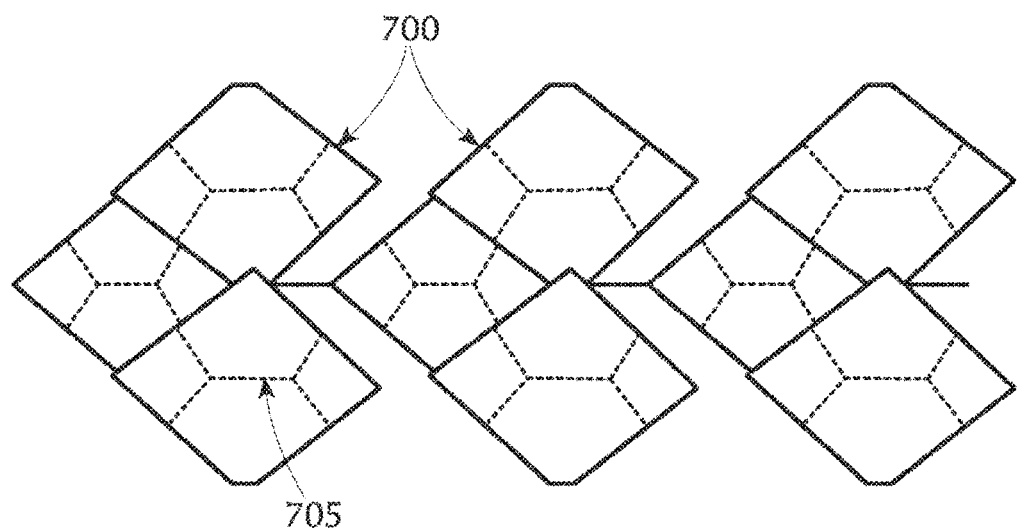
FIG. 7A is a plan view while in an unrolled, flat state of the dual structure assembly mechanical thrombectomy device in accordance with the present invention; wherein the outer cage and inner component are manufactured from a single cut tube or cut pattern.
Figure 7C:
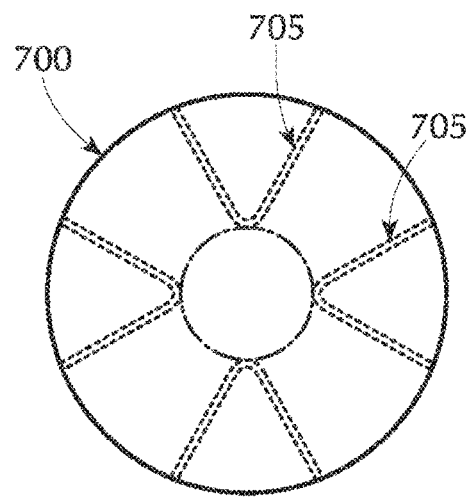
FIG. 7C is a radial cross-sectional view of the dual structure assembly mechanical thrombectomy device of FIG. 7B along lines VIIC-VIIC.
Figure 7B:
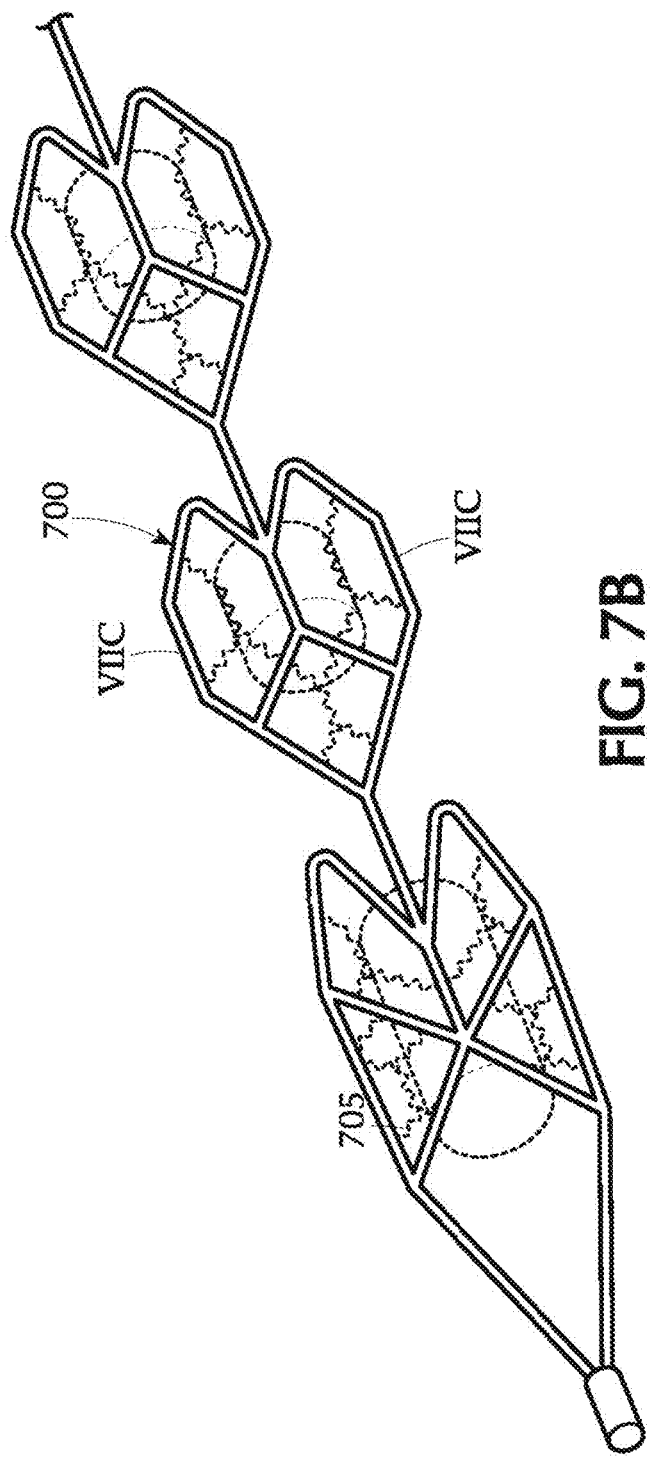
FIG. 7B is an isometric view while in the expanded state of the dual structure assembly mechanical thrombectomy device of FIG. 7A.

The outer cage 305 and wave-shape component 310 differing in diameter, as depicted in FIGS. 3A-3C, are each manufactured from two separately cut tubes or cut patterns of different diameters thereafter assembled together to form the dual structure assembly. Alternatively, the present invention contemplates the outer cage and inner component being formed or manufactured from a single cut tube or cut pattern, rather than two separately cut tubes or cut patterns. A single cut tube or cut pattern used to form both the primary and secondary struts in accordance with the present invention reduces the overall cost of manufacture while maintaining the benefits associated with the dual structure assembly (e.g., outer cage and inner component). Specifically, the single cut tube or cut pattern is deformed and heat set into the inner component and the outer cage, respectively, with the same benefits and advantages discussed above with respect to the two separately cut tubes or cut patterns then assembled together. FIG. 7A depicts part of the single cut tube or cut pattern while in an unrolled (flattened) state. This novel configuration of the dual structure assembly manufactured from a single cut tube or cut pattern is achieved by primary struts 700 forming the outer cage component being expanded and heat set to a primary diameter approximately 3.0 mm—approximately 6.0 mm (preferably, approximately 5.0 mm) while the secondary struts 705 comprising the inner component are expanded and heat-set to form a circular channel having a smaller secondary diameter approximately 1.0 mm-approximately 3.0 mm (preferably, approximately 1.25 mm), during respective expansion steps. FIG. 7B is an isometric view of the dual structure assembly formed from a single cut tube or cut pattern while in a rolled expanded state, wherein the assembly includes formed primary struts 700 defining an outer cage and inwardly radially deformed secondary struts 705 comprising the inner component defining a cylindrical channel. A radial cross-sectional view of the dual structure assembly of FIG. 7B along lines VIIC-VIIC is illustrated in FIG. 7C.

Alternatively, the single cut tube or cut pattern may have a diameter equal to the preferred expanded diameter of the primary struts 700 forming the outer cage (e.g., approximately 5.0 mm) and a heat-set process applied to reduce in diameter (e.g., approximately 1.25 mm) the single cut tube or cut pattern to form the secondary struts 705 of the inner component. Thus, no expansion nor reduction in diameter of the single cut tube or cut pattern is necessary to form the primary struts of the outer cage. Accordingly, a single raw material cut tube or cut pattern (e.g., Nitinol) can be varied to any desired preferential primary and secondary diameter, respectively, to form the outer cage and inner component of the dual structure assembly mechanical thrombectomy device.

Figure 14:
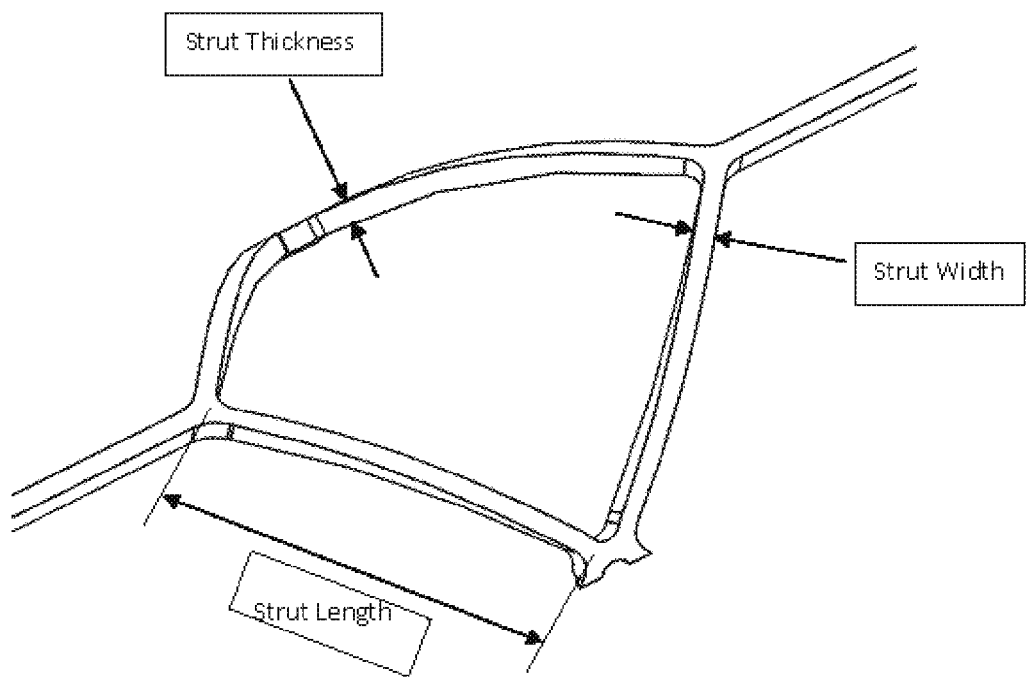
FIG. 14 is an illustration of an exemplary strut of the mechanical thrombectomy device to define the measurements of strut length, width and thickness.

It is further desirable for the dual structure assembly mechanical thrombectomy device to collapse/reduce/wrap-down sufficiently small in diameter to be receivable within a smaller size (e.g., approximately 0.017") microcatheter. However, mechanical thrombectomy devices that collapse to smaller diameter sizes face several challenges. In order to allow construction of the proximal bond of the dual structure mechanical thrombectomy device and ensure an appropriate device crossing profile (i.e., cross-sectional area) (preferably less than approximately 0.0165" for compatibility with 0.017" microcatheters), a smaller diameter Nitinol cut tube raw material is preferred. An inherent problem to be solved or overcome in accordance with the present invention when utilizing smaller diameter cut tube raw material is accommodation of sufficient strut width and thickness for the outer cage to exert sufficient radial force when engaging the clot in the vessel to restore blood flow and facilitate clot removal. Wherein the measurements of strut length, width and thickness are defined by the illustration in FIG. 14.

Figure 8C:
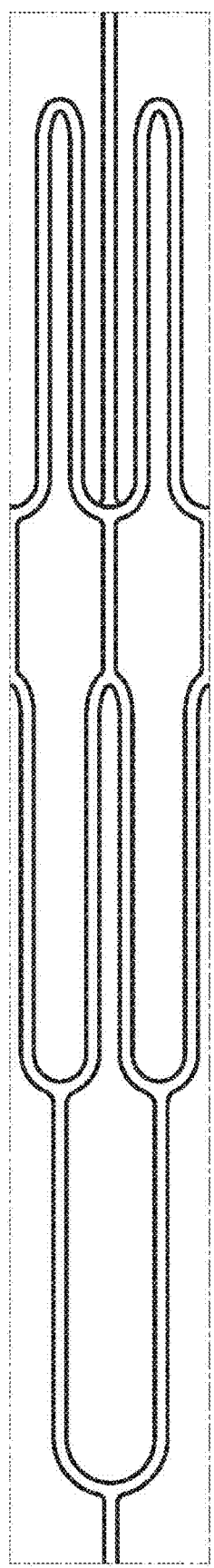
FIG. 8C is a flat, unrolled view of a radial section of the proximal first cell/segment outer cage of FIG. 8A with the connector strut between the first and distal second cell/segment of the outer cage identified, this connector strut may be eliminated in the distal second section to maximize adjacent strut widths.

It is therefore desirable to maximize strut width to exert sufficient radial force while simultaneously configuring the outer cage to efficiently wrap down reducing in diameter to be receivable within a smaller size microcatheter (e.g., 0.017" microcatheter). To achieve these goals, the present inventive mechanical thrombectomy device has a multi-component assembly 800 (as seen in FIGS. 8A & 8B, depicting exploded and assembled views, respectively) including: an outer cage 805, a wave-shape component 810 (similar to that shown in FIGS. 2A-2D) and an expanded distal tapered-end mesh section 815. In the illustrative example shown in FIG. 8A, outer cage 805 is preferably a 2-segment design or configuration (i.e., 2-segment outer cage 805 comprising a first segment 890 connected to a second segment 890' by a connector strut 895); however other configurations are contemplated and within the intended scope of the present invention. Outer cage 805 may be manufactured from a raw material (e.g., Nitinol) cut tube having a diameter of approximately 0.36 mm to approximately 2.0 mm to provide appropriate strut geometry. The wave-shape component 810 may be manufactured from a smaller diameter (approximately 0.15 mm) raw material (e.g., Nitinol) cut tube to facilitate efficient wrapping of the device during loading into a microcatheter, and assembly of the proximal joint with a profile compatible with 0.017" microcatheters. In particular, maximization of strut width of the outer cage 805 in the multi-component configuration of FIGS. 8A & 8B is realized by having the wave-shape component 810 form a wave pattern (similar to that shown in FIGS. 2A-2D) expand or extend axially into the distal section which contains a distal fragment protection member (e.g., expanded distal tapered-end mesh section 815). In addition, the connector strut 895 connecting the second segment 890' of the outer cage 805 to the expanded distal tapered-end mesh section 815 (as depicted in FIG. 8C) has been eliminated, replaced by the wave-shape component 810. Elimination of the connector strut also optimizes efficiency of wrap-down of the outer cage to be receivable within smaller size microcatheters (e.g., 0.017" microcatheters). The strut 895 connecting the second segment 890' of the outer cage 805 to the distal mesh section 815 is able to be eliminated in the present inventive configuration because the expanded distal tapered-end mesh section 815 is attached directly to the wave-shape component 810 providing a distal fragment protection zone and also serving as a distal anchor for intermediate catheter support during the procedure, rather than the outer cage 805. Functionality provided by the outer cage and wave-shape component have been discussed in detail above. The expanded distal tapered-end mesh section 815 maintains the clot in place during retrieval so that it does not fragment. Preferably, the laser cut tube forming the expanded distal tapered-end mesh section has a reduced diameter to aid in securing it on its closed distal end 820.

Figures 9A, 9B:
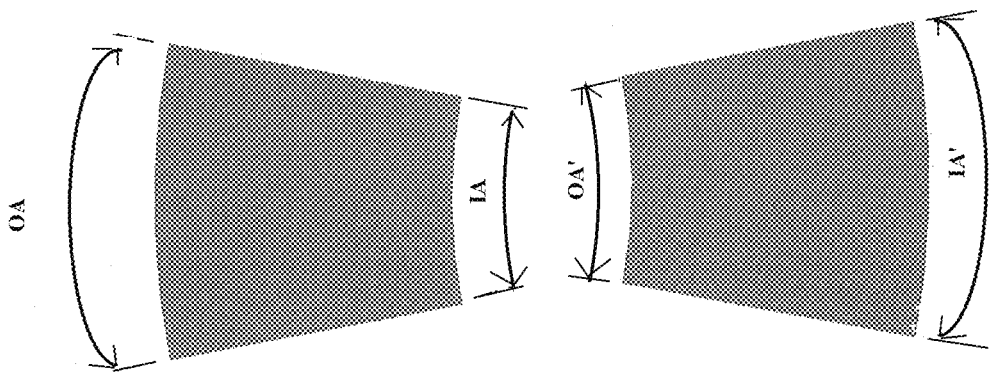
FIG. 9A is a prior art strut cross-section geometry of a single wedge shape strut comprising a stent laser cut from a Nitinol tube.
FIG. 9B is a strut cross-section geometry of a single wedge shape strut of a stent in accordance with the present invention laser cut from a Nitinol concave sheet.

During manufacture of conventional mechanical thrombectomy devices, a laser beam used to cut a desired tube pattern remains stationary while a raw material (e.g., Nitinol) cut tube forming the stent is rotated. FIG. 9A represents a standard or conventional strut cross-section geometry when laser cut from a raw material tube (e.g., Nitinol tube). Rotation is guided or dictated by the desired laser cut flat pattern.

As is clearly evident from FIG. 9A, the radial cross-section of the conventional wedge shape strut is widest along its outer surface (e.g., outer diameter) and tapers smaller until reaching its inner surface (e.g., inner diameter). That is, the conventional wedge shape strut has a smallest arc length (i.e., measure of the distance along the curved line making up the inner arc) denoted as "IA" along the inner surface (inner arc forming the inner diameter of the tube) and a largest arc length (i.e., measure of the distance along the curved line making up the outer arc) denoted as "OA" along the outer surface of the cross-section (outer arc forming the outer diameter of the tube). In other words, the arc length increases from the inner surface (inner diameter of the tube) to the outer surface (outer diameter of the tube). Accordingly, the arc length is longest (greatest contact surface area) along the outer surface (OA) of the radial cross-section of the conventional strut and the arc length is shortest (smallest contact surface area) along the inner surface (IA) of the cross-section of the conventional strut. Such conventional design results in an outward radial force of the stent being applied over a larger surface area, hence reducing outward radial pressure per strut surface area and clot embedding. Enhanced or improved embedding of the clot in the mechanical thrombectomy device may be realized in accordance with the present invention by modifying the strut geometry of the outer cage, specifically reducing the contact surface area of the outer surface (OA).

Figure 10:
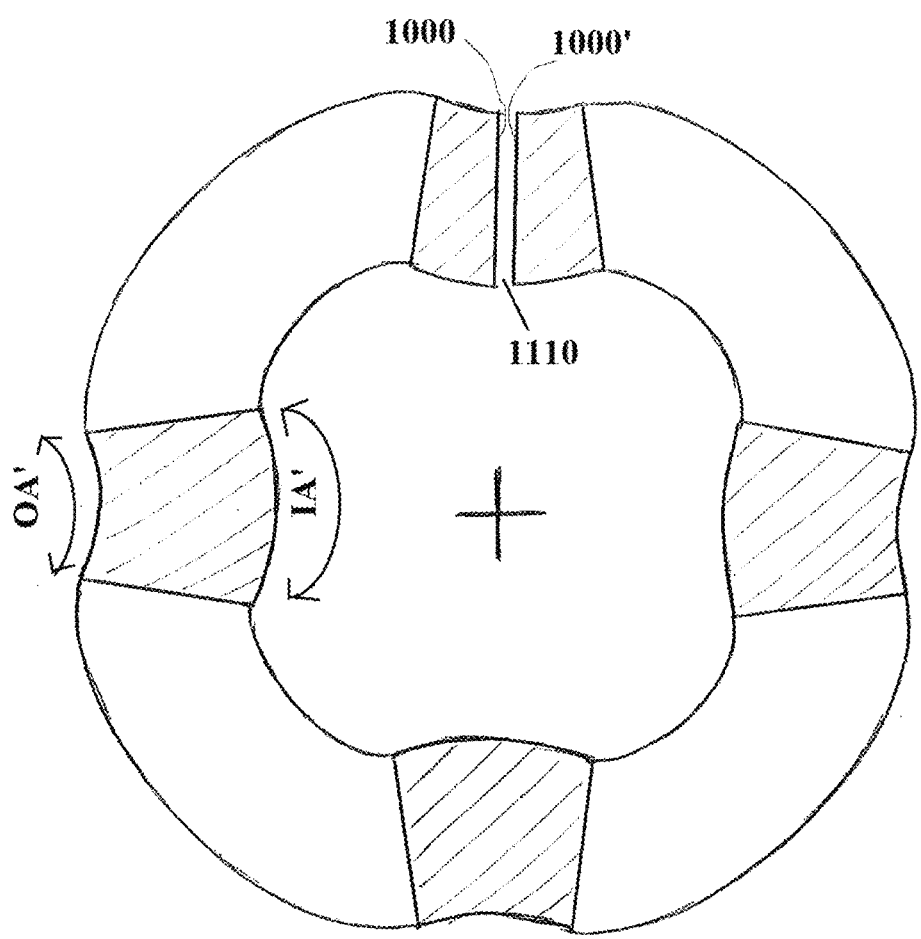
FIG. 10 is a radial cross-sectional view depicting the longitudinal slit or open seam of the everted laser cut concave sheet or plate deformed about a mandrel and heat set, wherein each strut has a cross-sectional geometry shown in FIG. 9B.

Rather than being cut from the Nitinol tube, as was the conventional strut cross-section depicted in FIG. 9A, in accordance with the present invention, the desired pattern of the stent may be laser cut on a concave Nitinol sheet or plate, while rotation of the concave sheet is controlled in an X-Y plane. FIG. 9B depicts the present inventive radial cross-section geometry of a laser cut single strut of an everted concave Nitinol sheet. To achieve this geometry, a desired pattern is laser cut in the concave Nitinol sheet or plate. Thereafter, the laser cut concave Nitinol sheet or plate is everted (turned inside out), formed around a mandrel of the desired diameter drawing the free edges towards one another to form a radial stent, and heat set to maintain this shape. FIG. 10 illustrates a radial cross-sectional view of the configured stent after the everted laser cut concave Nitinol sheet or plate has been wrapped about a mandrel, shape set to form a tube, and its opposing longitudinal edges 1000, 1000' drawn toward one another to define a longitudinal slit or open seam 1110 allowing overlap when the stent is wrapped-down/reduced in diameter. Alternatively, the opposing longitudinal edges can be joined together, e.g., laser welded, soldered or similar mechanical joining process.

Contrary to that of the conventional cross-section wedge shape strut laser cut from a Nitinol tube (FIG. 9A), the present inventive laser cut concave Nitinol sheet forms a wedge shape strut that is widest along its inner surface (inner diameter) and tapers smaller until reaching its outer surface (outer diameter), as seen in FIG. 9B. That is, the present inventive wedge shape strut has a largest arc length (i.e., measure of the distance along the curved line making up the outer arc) denoted as (IA') along the inner surface (inner arc forming the inner diameter of the tube) and a smallest arc length (i.e., measure of the distance along the curved line making up the outer arc) denoted as (OA') along the outer surface of the cross-section (outer arc forming the outer diameter of the tube). Hence, the arc length decreases from the inner surface (IA') to the outer surface (OA'). Accordingly, the arc length is shortest (smallest contact surface area) along the outer surface (OA') of the cross-section of the present inventive strut and the arc length is longest (largest contact surface area) along the inner surface (IA') of the cross-section of the present inventive strut. Such novel strut design results in maintaining an outward radial force of the stent being applied over a smaller or reduced contact surface area of the outer surface (OA') in contact with the clot than the contact surface area of the outer surface (OA) of the conventional strut depicted in FIG. 9A, hence increasing outward radial pressure and clot embedding.

Figure 11B:
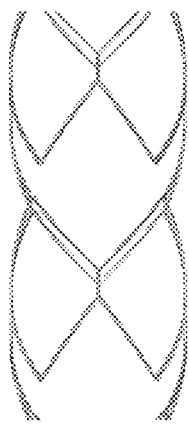
FIG. 11B is a partial longitudinal view of the present inventive device laser cut from a Nitinol concave sheet rolled about the mandrel depicting the seam in the body segments along the connection struts without eyelets.
Figure 11B:
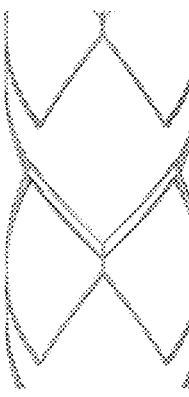
Figure 11A:
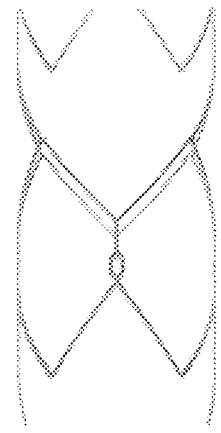
FIG. 11A is a partial longitudinal view of the present inventive device laser cut from a Nitinol concave sheet rolled about the mandrel depicting the seam in the body segments along the connection struts with eyelets.
Figure 11A:
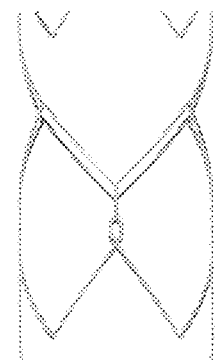

FIG. 11A is a partial longitudinal view of the present inventive laser cut Nitinol concave sheet of a stent with eyelets, rolled about the mandrel depicting the laser welded seam in the body segments aligned with the connection struts along the center-line of the device. While FIG. 11B is a similar view of the present inventive laser cut Nitinol concave sheet of a stent without eyelets. The seam may be welded or soldered to form a cylindrical device from the inverted laser cut concave sheet. If eyelets are included in the body segments/cells of the stent (FIG. 11A), the eyelet may be closed by laser welding the seam together.

Figure 12A:
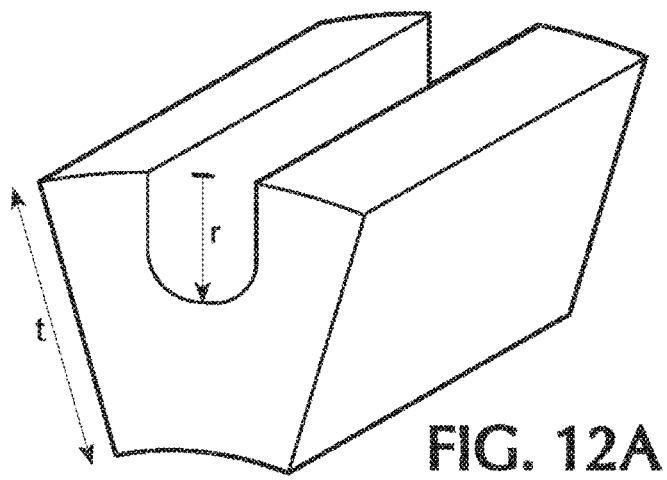
FIG. 12A a perspective view of a strut laser cut from a Nitinol tube, wherein a notch, groove or channel is cut into or removed from the outer diameter surface of the strut thereby reducing the outer surface contact area of the strut.
Figure 13A:
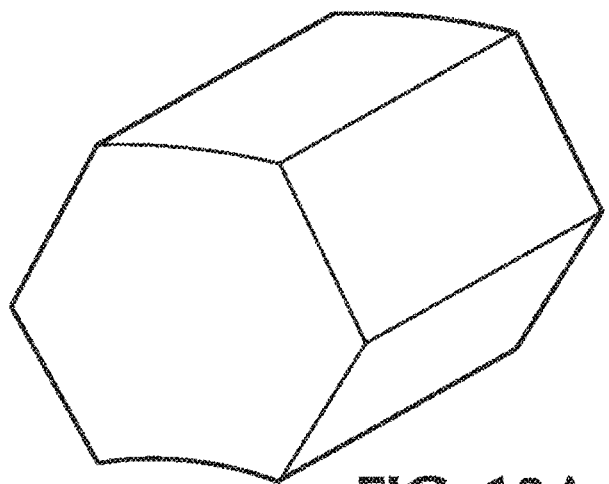
FIG. 13A is a perspective view of another configuration of a strut laser cut from a Nitinol tube having chamfered cuts to the corners of the outer surface (outer diameter) of the strut thereby reducing the outer surface contact area of the strut.
Figure 13C:
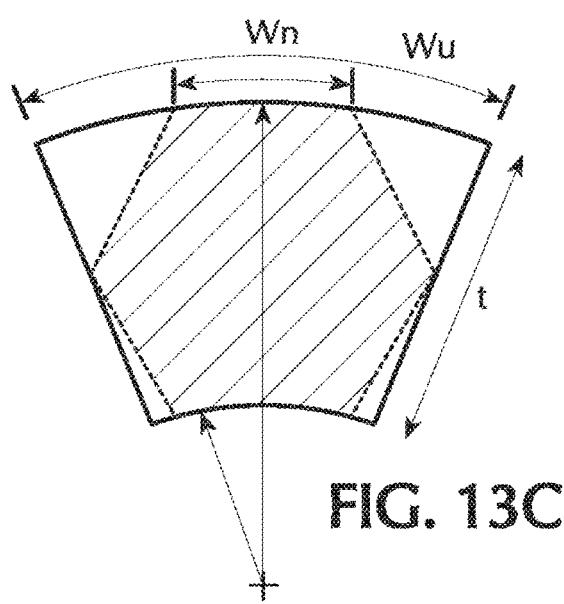
FIG. 13C is an end view of the strut of FIG. 13A illustrating by dashed lines the corners that have been removed.
Figure 12B:
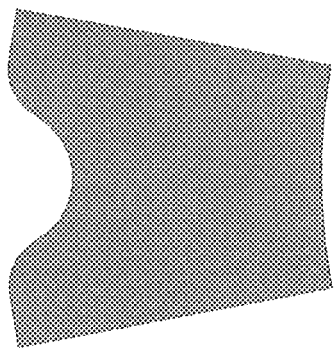
FIG. 12B is an end view of the strut of FIG. 12A.
Figure 13B:
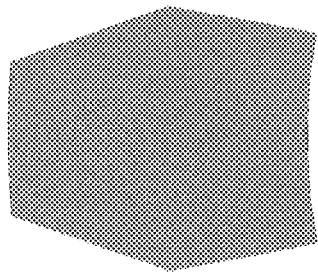
FIG. 13B is an end view of the strut of FIG. 13A.

Another novel way to realize the aforementioned goal of reducing the strut contact surface area along the outer surface (outer diameter) of the stent is by removing a portion of the outer surface (outer diameter) from the cut tubing. In FIGS. 12A & 12B, a notch, groove or channel is cut into or otherwise removed (e.g., grinding) from the outer diameter surface of the Nitinol tubing strut thereby reducing the contact surface area along its outer surface (outer diameter) with that of the clot. The notch, groove or channel may be a predefined radius, V-shaped, U-shaped or any other desired shape. Despite removing a portion of the outer surface (outer diameter) of the strut, if desired, the thickness of the strut can be increased to maintain the overall cross-sectional area of the strut. The two thinner struts formed along the outer surface or profile (outer diameter) on either side of the notch, groove or channel each has a smaller contact surface area (in comparison to the outer surface area without the notch, groove or channel) promoting the clot to more easily to embed. Alternatively, or in combination therewith, a chamfer edge or secondary off-axis cut can be made in each corner of the outer surface (outer diameter) of the Nitinol tubing strut, as shown in FIGS. 13A-13C, once again with the shared goal of reducing the outer surface contact area of the strut. Referring to the end view of the Nitinol tubing formed strut in FIG. 13C the removal of the corners (denoted by dashed lines) reduces the overall contact surface area arc length along the outer surface (outer diameter) from a conventional prior art width $L_0$ (before making the secondary cuts) to the present inventive reduced arc length $L_1$ (after making the secondary cuts). What results is depicted in the end and perspective views shown in FIGS. 13A & 13B, respectively, having a reduced contact surface area along the outer surface (outer diameter) of the strut.

Each of the present inventive geometry strut configurations may be used independently or in any combination thereof to improve clot removal performance by improving embedding of the clot in the thrombectomy device. Also, features associated with some aspects of the present inventive mechanical thrombectomy device are applicable for use in a wide range of different size catheters, even those having a relatively small diameter.

The present inventive device has been illustrated and described for use in a mechanical thrombectomy procedure but is applicable for use in other intravascular medical procedures in which a self-expanding mesh, cage, scaffolding or skeleton is utilized.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A self-expanding intravascular medical device, comprising:
    a multi-component assembly comprising:
        a self-expanding outer cage component comprising a plurality of struts; and
        a single cell wave-shape component disposed within the self-expanding outer cage component forming a channel therein, wherein a proximal end of the single cell wave-shape component is connected to the self-expanding outer cage component at a proximal joint; the single cell wave-shape component including a series of directly connected single cells each of the single cells defined by two struts interconnected at two points of intersection.

2. The self-expanding intravascular medical device according to claim 1, wherein the self-expanding outer cage component is formed by a plurality of asymmetrically arranged struts.

3. The self-expanding intravascular medical device according to claim 1, wherein the single cell wave-shape component is a mesh forming the series of directly connected single cells, the series of connected single cells varying in size and forming a wave shape varying in amplitude.

4. The self-expanding intravascular medical device according to claim 1, wherein the single cell wave-shape component is a mesh forming the series of directly connected single cells uniform in size and forming a wave shape varying in amplitude.

5. The self-expanding intravascular medical device according to claim 1, wherein each of the self-expanding outer cage component and the single cell wave-shape component differ in diameter and are formable from a single cut tube or cut pattern; wherein the single cut tube or cut pattern is expandable to a primary diameter to form primary struts of the self-expanding outer cage component, while the single cut tube or cut pattern is expandable to a secondary diameter smaller than the primary diameter to form secondary struts of the single cell wave-shape component.

6. The self-expanding intravascular medical device in accordance with claim 1, wherein the self-expanding outer cage component has a distal fragment protection member disposed on a distal end of the self-expanding outer cage component.

7. The self-expanding intravascular medical device in accordance with claim 6, wherein the distal fragment protection member is a mesh comprising a plurality of interconnected struts or a clump of intertwined strands.

8. The self-expanding intravascular medical device in accordance with claim 6, wherein the distal end of the self-expanding outer cage component is attached to the distal fragment protection member, while the distal end of the single cell wave-shape component is not connected to the distal fragment protection member.

9. The self-expanding intravascular medical device in accordance with claim 6, wherein the single cell wave-shape component is a mesh forming the series of directly connected single cells in a pattern in which the single cells are twisted relative to each other about a central axis extending longitudinally through the channel of the single cell wave-shape component such that some of the intersections of the single cells are not aligned with the central axis.

10. The self-expanding intravascular medical device in accordance with claim 1, wherein the distal end of the single cell wave-shape component is attached to a distal fragment protection member, while the distal end of the self-expanding outer cage is not connected to the distal fragment protection member.

11. The self-expanding intravascular medical device in accordance with claim 1, further comprising an expanded distal tapered-end mesh section; wherein the expanded distal tapered-end mesh section is attached directly to the single cell wave-shape component; and there is no direct physical connection between the expanded distal tapered-end mesh section and the self-expanding outer cage component.

12. The self-expanding intravascular medical device in accordance with claim 11, wherein the self-expanding outer cage component has a primary diameter and the single cell wave-shape component forms a wave shape of circular cross-section having a secondary diameter smaller than that of the primary diameter.

13. The self-expanding intravascular medical device in accordance with claim 1, wherein the channel as defined by the series of directly connected single cells is free of any internal obstruction.

14. A self-expanding intravascular medical device, comprising:
    a multi-component assembly comprising:
        a self-expanding outer cage component comprising a plurality of struts; and
        an inner component disposed within the self-expanding outer cage component forming a cylindrical channel therein, wherein a proximal end of the inner component is connected to the self-expanding outer cage component at a proximal joint; wherein the inner component is a single cell wave-shape component including a series of directly connected single cells each of the single cells defined by two struts interconnected at two points of intersection;
        wherein each of the self-expanding outer cage component and a circular cross-section of the cylindrical channel formed by the inner component differ in diameter and are formable from a single cut tube or cut pattern; wherein the single cut tube or cut pattern has a primary diameter equal to an expandable diameter of primary struts forming the self-expanding outer cage component while the single cut tube or cut pattern is heat settable to a secondary diameter smaller than the primary diameter to form the circular cross-section of the cylindrical channel formed by the inner component; and wherein the proximal end of the inner component does not extend in a proximal direction beyond a proximal end of the self-expanding outer cage component.

* * * * *